United States Patent
Yerva et al.

(10) Patent No.: US 11,874,879 B2
(45) Date of Patent: *Jan. 16, 2024

(54) DEEP MULTI-MODAL PAIRWISE RANKING MODEL FOR CROWDSOURCED FOOD DATA

(71) Applicant: MYFITNESSPAL, INC., San Francisco, CA (US)

(72) Inventors: Surender Reddy Yerva, San Francisco, CA (US); Iman Barjasteh, San Francisco, CA (US); Patrick Howell, San Francisco, CA (US); Chul Lee, San Francisco, CA (US); Hesamoddin Salehian, San Francisco, CA (US)

(73) Assignee: MyFitnessPal, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/459,404

(22) Filed: Aug. 27, 2021

(65) Prior Publication Data

US 2021/0390139 A1 Dec. 16, 2021

Related U.S. Application Data

(63) Continuation of application No. 16/354,863, filed on Mar. 15, 2019, now Pat. No. 11,106,742.

(Continued)

(51) Int. Cl.
*G06F 16/906* (2019.01)
*G16H 20/60* (2018.01)
(Continued)

(52) U.S. Cl.
CPC .......... *G06F 16/906* (2019.01); *G06F 16/908* (2019.01); *G06F 16/90344* (2019.01);
(Continued)

(58) Field of Classification Search
CPC .......... G06N 20/00; G06N 5/02; G06N 5/022
See application file for complete search history.

(56) References Cited

U.S. PATENT DOCUMENTS

2015/0228062 A1 8/2015 Joshi et al.
2019/0027060 A1 1/2019 Ishii
(Continued)

OTHER PUBLICATIONS

Hang, L., "A short introduction to learning to rank," IEICE Transactions on Information and Systems, 2011, pp. 1854-1862, vol. 94, No. 10.

(Continued)

*Primary Examiner* — Hau H Hoang
(74) *Attorney, Agent, or Firm* — Maginot, Moore & Beck, LLP

(57) ABSTRACT

A method and system for providing more relevant search results and recommendation from a food database is disclosed. The method includes receiving a query, a first candidate food, and a second candidate food. The method includes generating vectors based on the query and food names of the first and second candidate foods using at least one embedding function of a machine learning model. The method includes determining nutrition content vectors from the nutritional data of the first and second candidate foods. The method includes generating a nutrition content vector based on the query using another embedding function of the machine learning model. The method includes determining which of the first and second candidate food is more relevant to the query based at least in part on the nutrition content vectors. The method includes providing search results or recommendation based on the determined relevance.

18 Claims, 9 Drawing Sheets

Related U.S. Application Data

(60) Provisional application No. 62/643,919, filed on Mar. 16, 2018.

(51) Int. Cl.
    *G06F 16/903* (2019.01)
    *G06N 3/049* (2023.01)
    *G06F 16/908* (2019.01)
    *G06N 20/10* (2019.01)

(52) U.S. Cl.
    CPC ............. *G06N 3/049* (2013.01); *G06N 20/10* (2019.01); *G16H 20/60* (2018.01)

(56) References Cited

U.S. PATENT DOCUMENTS

2019/0057306 A1    2/2019    Xue et al.
2019/0171707 A1*  6/2019    Rapaport ............... G06F 16/951

OTHER PUBLICATIONS

Li, H., "Learning to rank for information retrieval and natural language processing," Synthesis Lectures on Human Language Technologies, vol. 7, No. 3, pp. 1-121, 2014.
Lecun, Y., Bottou, L., Bengio, Y., and Haffner, P., "Gradient-based learning applied to document recognition," Proceedings of the IEEE, 1998, pp. 2278-2324, vol. 86, No. 11.
Krizhevsky, A., Sutskever, I., and Hinton, G. E., "Imagenet classification with deep convolutional neural networks," in Advances in neural information processing systems, 2012, pp. 1097-1105.
Wang, J., Song, Y., Leung, T., Rosenberg, C., Wang, J., Philbin, J., Chen, B., and Wu, Y., "Learning fine-grained image similarity with deep ranking," in Proceedings of the IEEE Conference on Computer Vision and Pattern Recognition, 2014, pp. 1386-1393.
Zhao, F., Huang, Y., Wang, L., and Tan, T., "Deep semantic ranking based hashing for multi-label image retrieval," in Proceedings of the IEEE Conference on Computer Vision and Pattern Recognition, 2015, pp. 1556-1564.
Zhao, X., Li, X., and Zhang, Z., "Multimedia retrieval via deep learning to rank," IEEE Signal Processing Letters, 2015, pp. 1487-1491, vol. 22, No. 9.
Severyn, A., and Moschitti, A., "Learning to rank short text pairs with convolutional deep neural networks," in Proceedings of the 38th International ACM SIGIR Conference on Research and Development in Information Retrieval, 2015, pp. 373-382, ACM.
Lu, Z., and Li, H., "A deep architecture for matching short texts," in Advances in Neural Information Processing Systems, 2013, pp. 1367-1375.
Rigutini, L., Papini, T., Maggini, M., and Bianchini, M., "A neural network approach for learning 409 object ranking," in International Conference on Artificial Neural Networks, 2008, pp. 899-908, Springer.
Gong, Y., Jia, Y., Leung, T., Toshev, A., and Ioffe, S., "Deep convolutional ranking for multilabel image annotation," 2013.
Zhang, X., Zhao, J., and Lecun, Y., "Character-level convolutional networks for text classification," in Advances in Neural Information Processing Systems, 2015, pp. 649-657.
Cao, Z., Wei, F., Dong, L., Li, S., and Zhou, M., "Ranking with recursive neural networks and its application to multi-document summarization.," in AAAI, 2015, pp. 2153-2159.
Mao, J., Xu, W., Yang, Y., Wang, J., Huang, Z., and Yuille, A., "Deep captioning with multimodal recurrent neural networks (m-rnn)," 2014.
Kiros, R., Salakhutdinov, R., and Zemel, R. S., "Unifying visual-semantic embeddings with multimodal neural language models," 2014.
Sutskever, I., Vinyals, O., and Le, Q. V., "Sequence to sequence learning with neural networks," in Advances in neural information processing systems, 2014, pp. 3104-3112.
Sundermeyer, M., Schluter, R., and Ney, H., "Lstm neural networks for language modeling.," in Interspeech, 2012, pp. 194-197.
Wang, J., Yang, Y., Mao, J., Huang, Z., Huang, C., and Xu, W., "Cnn-rnn: A unified framework for multi-label image classification," in Proceedings of the IEEE Conference on Computer Vision and Pattern Recognition, 2016, pp. 2285-2294.
Frome, A., Corrado, G. S., Shlens, J., Bengio, S., Dean, J., Mikolov, T., et al., "Devise: A deep visual-semantic embedding model," in Advances in neural information processing systems, 2013, pp. 2121-2129.
Vinyals, O., Toshev, A., Bengio, S., and Erhan, D., "Show and tell: A neural image caption generator," in Proceedings of the IEEE Conference on Computer Vision and Pattern Recognition, 2015, pp. 3156-3164.
Lynch, C., Aryafar, K., and Attenberg, J., "Images don't lie: Transferring deep visual semantic features to large-scale multimodal learning to rank," 2015.
Howell, P. D., Martin, L. D., Salehian, H., Lee, C., Eastman, K. M., and Kim, J., "Analyzing taste preferences from crowdsourced food entries," in Proceedings of the 6th International Conference on Digital Health Conference, 2016, pp. 131-140, ACM.
Srivastava, A., Jermyn, I., and Joshi, S., "Riemannian analysis of probability density functions with applications in vision," in Computer Vision and Pattern Recognition, 2007. CVPR'07. 441 IEEE Conference on, 2007, pp. 1-8, IEEE.
Lee, J., "Riemannian geometry: An introduction to curvature, No. 176 in graduate texts in 443 mathematics," 1997.
Moakher, M., "A differential geometric approach to the geometric mean of symmetric positive definite matrices," SIAM Journal on Matrix Analysis and Applications, 2005, pp. 735-747 vol. 26, No. 3.
Hochreiter, S., and Schmidhuber, J., "Long short-term memory," Neural computation, 1997, pp. 1735-1780, vol. 9, No. 8.
Mikolov, T., Sutskever, I., Chen, K., Corrado, G., and Dean, J., "Efficient estimation of word representations in vector space," in Proceedings of Workshop at ICLR, 2013.
F. Chollet, "Keras: Theano-based deep learning library," Code: https://github. com/fchollet.459 Documentation: http://keras. io, 2015.
Wang, Y., Wang, L., Li, Y., He, D., and Liu, T.-Y., "A theoretical analysis of ndcg type ranking measures," in Conference on Learning Theory, 2013, pp. 25-54.
Matching Restaurant Menus to Crowdsourced Food Data a Scalable Machine Learning Approach by Hesam Salehian, 2017 ACM. 978-1-4503-4887—Apr. 17, 2008 (Year:2017).

\* cited by examiner

500

510 Receive a plurality of training inputs, each training input including (i) a query string, (ii) a first descriptive string and first nutritional data labeled as corresponding to a correct output, and (iii) a second descriptive string and second nutritional data labeled as corresponding to an incorrect output.

520 Generate (i) a first feature vector based on the first descriptive string, (ii) a second feature vector based on the second descriptive string, and (iii) a third feature vector based on the query string, using at least one first embedding function of a machine learning model, for each training input.

530 Generate (i) a first nutrition information vector from the first nutritional data and (ii) a second nutrition information vector from the second nutritional data, for each training input.

540 Generate a third nutrition information vector based on the query string, using a second embedding function of the machine learning model, for each training input.

550 Determine a hinge loss based on the first feature vector, the second feature vector, the third feature vector, first nutrition information vector, the second nutrition information vector, and the third nutrition information vector, for each training input.

560 Adjust parameter values of the machine learning model based on the hinge loss, for each training input.

FIG. 5

DEEP MULTI-MODAL PAIRWISE RANKING MODEL FOR CROWDSOURCED FOOD DATA

CROSS-REFERENCE TO RELATED APPLICATIONS

This application is a continuation of U.S. patent application Ser. No. 16/354,863, filed Mar. 15, 2019, now U.S. Pat. No. 11,106,742, which claims priority to U.S. provisional patent application No. 62/643,919, filed Mar. 16, 2018, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The methods and systems disclosed in this document relate health tracking systems having a food database and, more particularly, to a deep multi-modal pairwise ranking model for crowdsourced food data.

BACKGROUND

In recent years, health and fitness tracking applications that track food consumption have become very popular. Food consumption is important to a healthy lifestyle and a person's diet is well known to be related to various health conditions, such as diabetes and obesity to name a few. Health and fitness tracking applications allow users to set and achieve personalized health goals by tracking the foods and beverages that they consume. These applications enable users to gain insights that help them make smarter choices and create healthier habits. However, in many such health and fitness tracking applications, it is often cumbersome for users to find the specific foods and beverages that they wish to track. Accordingly, it would be advantageous to provide users with health tracking systems that provides highly relevant search results when a user searches for foods and beverages.

SUMMARY

In accordance with one exemplary embodiment of the disclosures, a method of operating a health tracking system is disclosed. The health tracking system has a processor and a database configured to store a plurality of data records, each of the plurality of data records comprising at least a descriptive string and nutritional data regarding a respective consumable item. The method comprises the steps of: receiving, with the processor, a query string; retrieving, with the processor, a first data record of the plurality of data records and a second data record of the plurality of data records from the database; generating, with the processor, (i) a first nutrition information vector from the nutritional data of the first data record and (ii) a second nutrition information vector from the nutritional data of the second data record; generating, with the processor, a third nutrition information vector based on the query string, using an embedding function of the machine learning model, the embedding function being learned in a training process of a machine learning model; and determining, with the processor, which of the first data record and the second data record is more relevant to the query string based at least in part on the first nutrition information vector, the second nutrition information vector, and the third nutrition information vector.

Pursuant to another exemplary embodiment of the disclosures, a health tracking system is disclosed. The health tracking system comprises: a database configured to store a plurality of data records, each of the plurality of data records comprising at least a descriptive string and nutritional data regarding a respective consumable item; and a data processor in communication with the database. The data processor is configured to: receive a query string; retrieve from the database a first data record of the plurality of data records and a second data record of the plurality of data records based on the query string; generate (i) a first nutrition information vector from the nutritional data of the first data record and (ii) a second nutrition information vector from the nutritional data of the second data record; generate a third nutrition information vector based on the query string, using an embedding function of the machine learning model, the embedding function being learned in the training process of the machine learning model; determining which of the first data record and the second data record is more relevant to the query string based at least in part on the first nutrition information vector, the second nutrition information vector, and the third nutrition information vector; and transmit a list of data records of the plurality of data records to an electronic device of a user of the health tracking system, the list of data records at least including the first data record and the second data record, a relative sorting of the first data record and the second data record in the list of data records depending on the determination of which of the first data record and the second data record is more relevant to the query string.

In accordance with yet another exemplary embodiment, a method of operating a health tracking system to train a machine learning model is disclosed. The method comprises the steps of: receiving, with a processor of the health tracking system, a plurality of training inputs, each training input including (i) a query string, (ii) a first descriptive string and first nutritional data labeled as corresponding to a correct output, and (iii) a second descriptive string and second nutritional data labeled as corresponding to an incorrect output; and for each training input: determining, with the processor, (i) a first nutrition information vector from the first nutritional data and (ii) a second nutrition information vector from the second nutritional data; generating, with the processor, a third nutrition information vector based on the query string, using an embedding function of the machine learning model; determining, with the processor, a hinge loss based at least in part on the first nutrition information vector, the second nutrition information vector, and the third nutrition information vector; and adjusting, with the processor, parameter values of the machine learning model based on the hinge loss.

These and other aspects of the disclosure shall become apparent when considered in light of the disclosure provided herein.

BRIEF DESCRIPTION OF THE DRAWINGS

The foregoing aspects and other features of a health and fitness tracking system are explained in the following description, taken in connection with the accompanying drawings.

FIG. 5 shows a method of operating the health tracking system to train the deep multi-modal pairwise ranking model.

Figure 1:
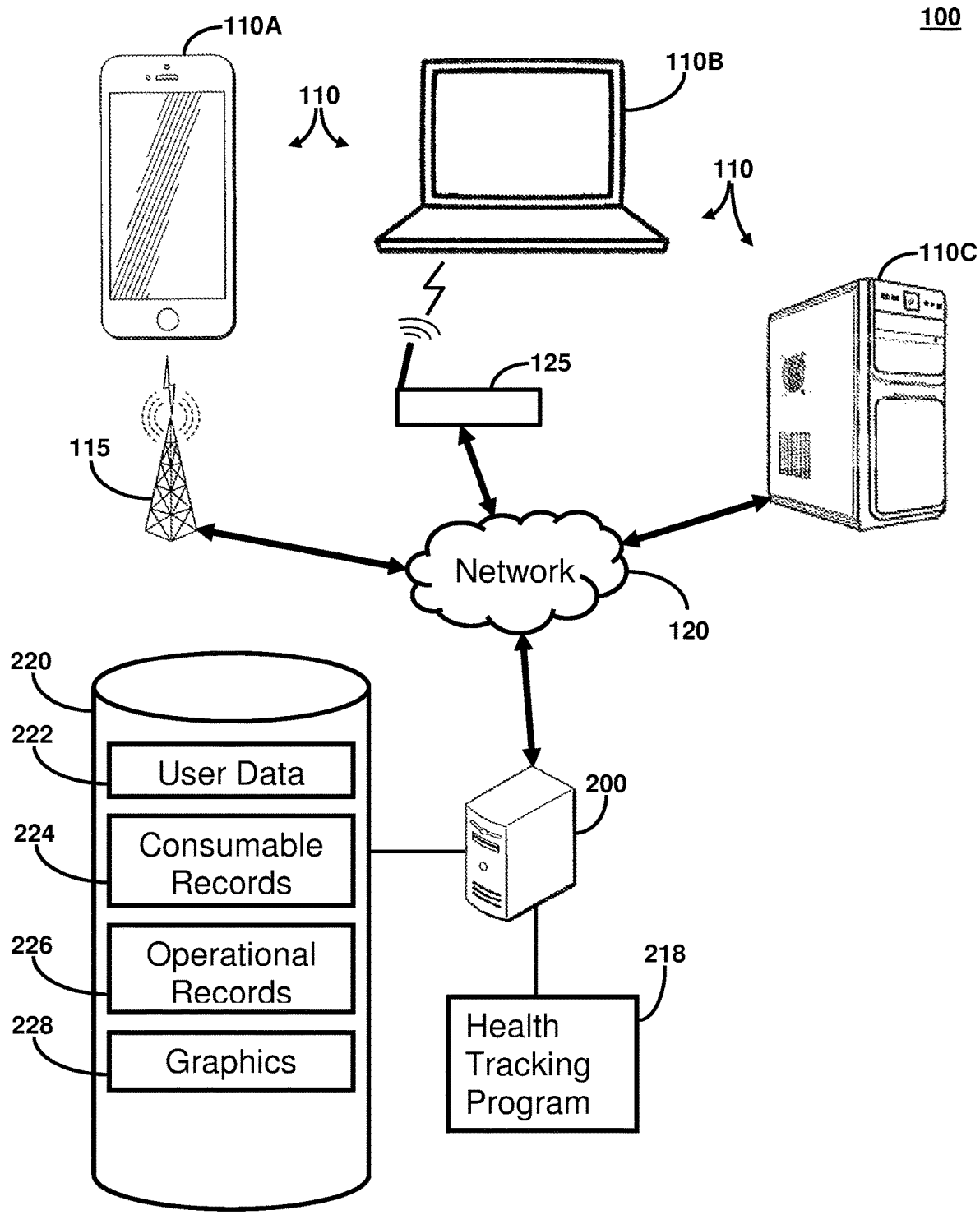
FIG. 1 shows a health tracking system.

All Figures© Under Armour, Inc. 2018. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" refers to foods, beverages, dietary supplements, vitamin supplements, medication, and other items for consumption. As used herein, the term "consumable record" refers to a database record that relates to a particular consumable. Each consumable record comprises a plurality of data fields that relate to a particular consumable item. In some embodiments, each consumable record includes a description field that includes data, such as a text string, that identifies or describes the particular consumable. In some embodiments, each consumable record includes an ingredients field that includes data, such as one or more text strings, that list ingredients for a particular consumable. In some embodiments, each consumable record includes fields for caloric content, macronutrients, micronutrients, serving size, and other nutrition and health information.

Health Tracking System

With reference to FIG. 1, an exemplary embodiment of a health tracking system 100 that utilizes deep multi-modal pairwise ranking of consumable records to provide more relevant search results and recommendations is shown. In the illustrated embodiment, the health tracking system 100 includes a plurality of health tracking devices 110 in communication with a system server 200 or other data processing system over a network 120 such as, e.g. the Internet.

The server 200 comprises a computerized device or data processing system configured to run one or more software applications on a processor thereof (e.g. the network-side health tracking program 218). The server 200 of the present embodiment is further configured to receive a plurality of consumable records which include item descriptions, as well as caloric and nutritional contents of a respective plurality of consumable items which are entered at the health tracking devices 110, other consumer devices, and/or provided from one or more manufacturing or distributing entities. The consumable records are stored at a storage apparatus or memory of the server 200 (e.g., consumable records 224).

The storage apparatus or memory is configured to store instructions including a network-side health tracking program 218 (which may also be referred to herein as the "health tracking application"), as well as a database 220 accessible by at least the health tracking program 218. The database 220 includes user data 222, consumable records 224, operational records 226, and graphics 228. Alternatively, the server 200 may be in communication with a separate storage entity (not shown) for storage thereof.

As will be discussed in further detail elsewhere herein, the server 200 utilizes at least one machine learning model to provide deep multi-modal pairwise ranking of consumable records. In one embodiment, the deep multi-modal pairwise ranking is used to provide more relevant search results when a user searches the consumable records 224. In one embodiment, the deep multi-modal pairwise ranking is used to provide more relevant recommendations of consumable records 224 to the user.

The health tracking devices 110 (which may also be referred to herein as "health and fitness tracking devices") comprise any number of computerized apparatus, which include a user interface, such as e.g., a smartphone 110A, laptop computer 110B, a tablet computer, a smart watch, a desktop computer 110C, or other such device. In at least one embodiment, the user interface may comprise an LCD touch screen or the like, a mouse or other pointing device, a keyboard or other keypad, speakers, and a microphone, as will be recognized by those of ordinary skill in the art. The user interface provides the user with any of various health, fitness and activity related data such as food and nutritional consumption, calorie expenditure, sleep metrics, weight, body fat, heart rate, distance travelled, steps taken, etc. In order to connect to the network 120, the health tracking devices 110 are generally configured to utilize any of various wired or wireless communications components, infrastructures and systems, such as cell towers 115 of a mobile telephony network, wireless routers 125, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices. Alternatively, or in addition, a user may manually enter health related data. Such sensors allow the user to easily track and automatically log activity and/or consumption information with the health tracking device. In addition, the health tracking device 110 may include one or more cameras configured to obtain health parameter data including e.g., capture images of a user's performance of an activity and/or capture images of consumed items or descriptions thereof (including barcodes or other machine readable identifiers).

The health tracking devices 110 are configured to communicate with the system server 200 in order to enable: accessing and searching of the consumable records 224 stored thereat, display of the consumable records, provide additional records, and/or enable the user to select individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 218, running on the processor (of the server 200) may be utilized to accomplish the foregoing, as explained in further detail below. A client-side software application for performing various functions necessary for the herein disclosed concepts may also be utilized (see health tracking application 316 of FIG. 3, discussed below).

System Server

Figure 2:
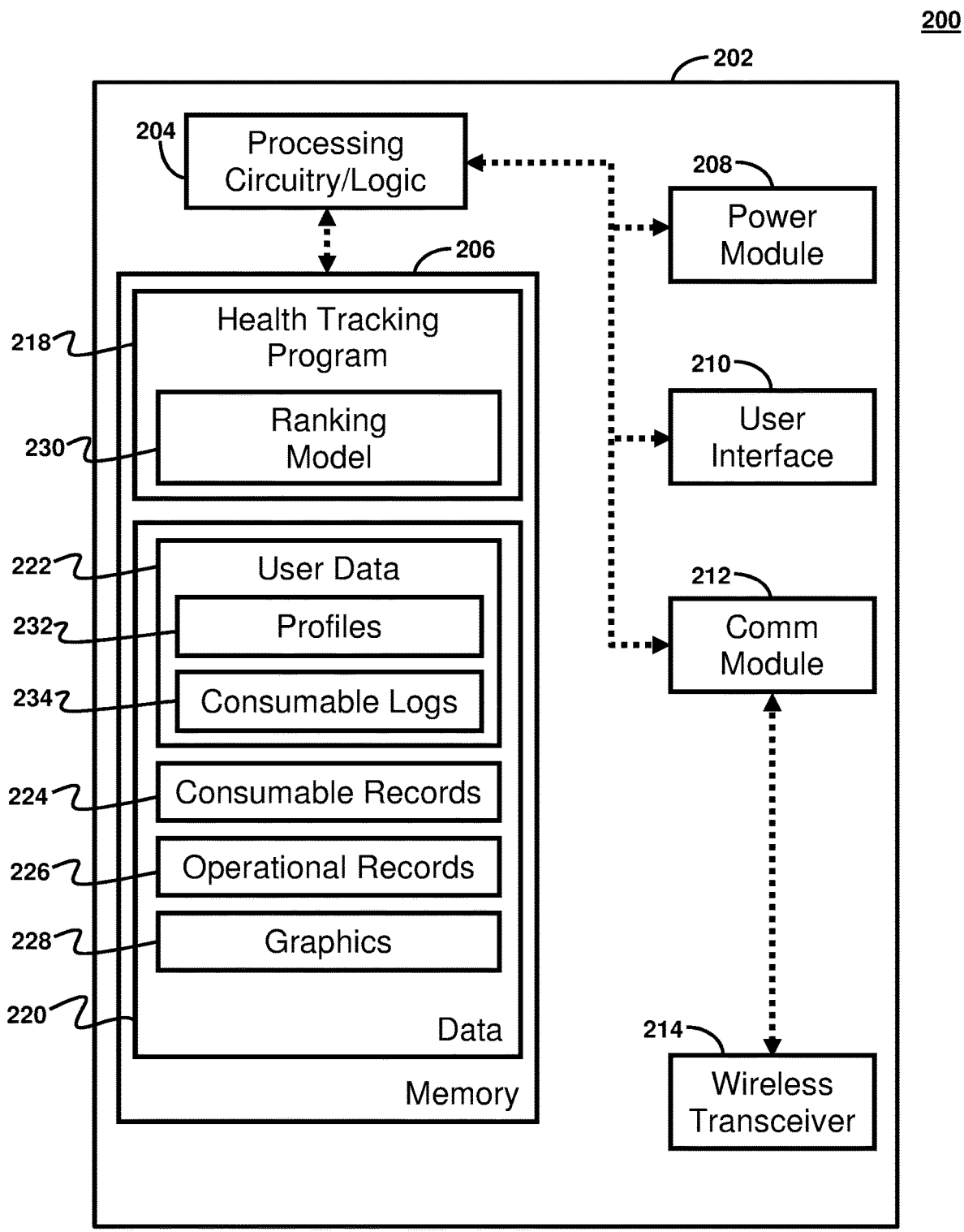
FIG. 2 shows a system server or data processing system of the health tracking system.

With reference now to FIG. 2, a block diagram of an exemplary embodiment of the system server 200 of FIG. 1 is shown. It is appreciated that the embodiment of the system server 200 shown in FIG. 2 is only one exemplary embodiment of a system server 200. As such, the exemplary embodiment of the system server 200 of FIG. 2 is merely representative of any of various manners or configurations of system servers or other data processing systems that are operative in the manner set forth herein.

The system server 200 of FIG. 2 is typically provided in a housing, cabinet or the like 202 that is configured in a typical manner for a server or related computing device. In one embodiment, the system server 200 includes processing circuitry/logic 204, memory 206, a power module 208, a user interface 210, a network communications module 212, and a wireless transceiver 214.

The processing circuitry/logic 204 is operative, configured and/or adapted to operate the system server 200 including the features, functionality, characteristics and/or the like as described herein. To this end, the processing circuitry/logic 204 is operably connected to the memory 206, the power module 208, the user interface 210, the network communications module 212, and the wireless transceiver 214. The memory 206 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 206 is configured to store instructions including a network-side health tracking application 218 for execution by the processing circuitry/logic 204, as well as a database 220 for use by at least the health tracking program 218. The database 220 includes user data 222, consumable records 224, operational records 226, and graphics 228. As discussed in greater detail below, the health tracking application 218 includes a multi-modal pairwise ranking model 230 configured to provide ranking of consumable records for the purpose of search and recommendation functions of the health tracking application 218.

With continued reference to FIG. 2, the power module 208 of the system server 200 is operative, adapted and/or configured to supply appropriate electricity to the system server 200 (i.e., including the various components of the system server 200). The power module 208 may operate on standard 120 volt AC electricity, but may alternatively operate on other AC voltages or include DC power supplied by a battery or batteries.

The network communication module 212 of the system server 200 provides an interface that allows for communication with any of various devices using various means. In particular, the network communications module 212 includes a local area network port that allows for communication with any of various local computers housed in the same or nearby facility. In some embodiments, the network communications module 212 further includes a wide area network port that allows for communications with remote computers over the Internet (e.g., network 120 of FIG. 1). Alternatively, the system server 200 communicates with the network 120 via a modem and/or router of the local area network. In one embodiment, the network communications module is equipped with a Wi-Fi transceiver 214 or other wireless communications device. Accordingly, it will be appreciated that communications with the system server 200 may occur via wired communications or via the wireless communications. Communications may be accomplished using any of various known communications protocols. In the embodiment of FIG. 2, the wireless transceiver 214 may be a Wi-Fi transceiver, but it will be recognized that the wireless transceiver may alternatively use a different communications protocol.

The system server 200 may be accessed locally by an authorized user (i.e., an administrator or operator). To facilitate local access, the system server 200 includes an interactive user interface 210. Via the user interface 210, an operator may access the instructions, including the health tracking application 218, and may collect data from and store data to the memory 206. In at least one embodiment, the user interface 210 may suitably include an LCD touch screen or the like, a mouse or other pointing device, a keyboard or other keypad, speakers, and a microphone, as will be recognized by those of ordinary skill in the art. Accordingly, the user interface 210 is configured to provide an administrator or other authorized user with access to the memory 206 and allow the authorized user to amend, manipulate and display information contained within the memory.

As mentioned above, the memory 206 includes various programs and other instructions that may be executed by the processor circuitry/logic 204. In particular, the memory 206 of the system server 200 of FIG. 2 includes the health tracking program 218 (which may also be referred to herein as a "health tracking application"). The health tracking program 218 is configured to cause the system server 200 to enable a user to obtain nutritional data related to any of various consumables. Execution of the health tracking application 218 by the processor circuitry/logic 204 results in signals being sent to and received from the user interface 210 and the communications module 212 (for further delivery to a user device such as a health tracking device 110), in order to allow the user receive and update various aspects of the consumable records 224. The network-side health tracking application 218 is configured to provide various graphical views and screen arrangements to be displayed to a user on a health tracking device 110.

The user data 222 includes at least user profiles 232 and corresponding consumable logs 234. The user profiles 232 include a profile data for each user of the health tracking system 100. Each user profile includes demographic information for the users such as name, age, gender, height, weight, performance level (e.g., beginner, intermediate, professional, etc.) and/or other information for the user. In at least one embodiment, the consumable logs 234 include a consumable diary/log for each user (which may also be referred to herein as a "food diary"). The consumable diary/log allows the user to track consumables that are consumed by the user over a period of days and any nutritional data associated with the food consumed. For example, the consumable diary/log may allow the user to enter particular consumable that is consumed by the user and keep track of the associated calories, macronutrients, micronutrients, sugar, fiber, and/or any of various other nutritional data associated with the consumables entered by the user in the consumable diary/log. In some embodiments, the user data 222 further includes various activity and fitness data collected by sensors (not shown) associated with the health tracking devices 110.

In an alternative embodiment, the foregoing profile data may be stored at a storage entity separate from yet in communication with the server 200. For example, a centralized server may be provided which is configured to store all data relating to an individual user in one storage area (including workout data, nutrition/consumption data, profile data, etc.).

A plurality of consumable records 224 is stored in the database 220. As discussed above, the term "consumable record" refers to a database record that relates to a particular consumable item. In at least one embodiment, each consumable record comprises a plurality of data fields that relate to a particular consumable item. In the disclosed embodiment, each of the consumable records includes a number of fields including, for example, a name for the consumable item, summary information about the consumable item, and detailed nutritional information about the consumable item. Detailed nutritional information about a consumable item may include one or more of: serving size, calories, nutrients, ingredients, or any other nutritional information about the item. For example, the detailed nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable may include some subset of the more detailed information about the consumable. For example, the summary information about the consumable may only include serving size and calorie information. The various fields of each consumable record may be populated by data from any user or third party data providers. Many, if not all, of consumable records 224 are created by users of the health tracking system 100 and/or have fields that are editable by users, without the need for special authorization or privileges. However, it will be recognized that in at least some embodiments, consumable records 224 may have been entered by any of various sources including an administrator or operator of the health tracking system 100, commercial food providers (e.g., food distributors, restaurant owners, etc.), and/or users of the health tracking system 100. In addition, certain information may be stored in a machine readable code (such as a bar code or QR code) which is captured via a camera or other scanner at the user device 110.

The operational records 226 include current and historical data stored by the system server 200 in association with operation of the system server 200, execution of the health tracking application 218, and/or manipulation of data 220 within the memory 206. For example, the operational records 226 may include information concerning amendments made to any of various consumable records 224. The operational records 226 may also include other information related to the control and operation of the system server 200, including statistical, logging, licensing, and historical information.

In one embodiment, graphical views 228 are provided at the server 200 which are pushed to the health tracking device 110 for display thereat of various screen arrangements.

While the system server 200 has been explained in the foregoing embodiment as housing the health tracking program 218 and the various records and databases in the memory 206, it will be recognized that in other embodiments these components may be retained in other one or more remote locations in communication with the health tracking system 100. For example, in at least one embodiment, the consumable records 224 may comprise data retained by a database separate from the system server 200. Alternatively, the consumable records 224 or certain fields of the consumable records 224 are received from a third party database. In such embodiments, the health tracking application may utilize any number of application programming interfaces (APIs) to access the data in the third party databases and incorporate such information for use in the health tracking application 218, without local storage thereof. Accordingly, it will be recognized that the description of the system server 200 of FIG. 2 is but one exemplary embodiment of a data processing system that may be utilized by the health tracking system 100.

A computer program product implementing an embodiment disclosed herein may therefore comprise one or more computer-readable storage media storing computer instructions executable by a processor to provide an embodiment of a system or perform an embodiment of a method disclosed herein. Computer instructions (e.g., the health tracking application 218 including the multi-modal pairwise ranking model 230) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium.

Health Tracking Devices

With reference again to FIG. 1, the health tracking devices 110 may be provided in any of various forms. Examples of a health tracking devices 110 configured for use with the health tracking system 100 include a smartphone 110A, a laptop computer 110B, and a desktop computer 110C, as shown in FIG. 1, as well as various other electronic devices. Accordingly, it will be recognized that the health tracking devices 110 may comprise portable electronic devices such as the smartphone 110A or the laptop computer 110B, or stationary electronic devices such as the desktop computer 110C. Other examples of health tracking devices include, handheld or tablet computers, smart watches, portable media players, other wearable devices, or any of various other health tracking devices configured to receive entry of consumables (not shown).

In one embodiment, data entered at one device 110 may be provided to other ones of the user's devices 110. For example, data entered at the smart phone 110A may be provided to the desktop computer 110C and/or the laptop computer 110B for storage thereat. Alternatively or in addition, the data may be stored at a single network storage apparatus (not shown) having a dedicated portion of storage for records relating to the user and accessible by all of the user's devices 110.

Figure 3:
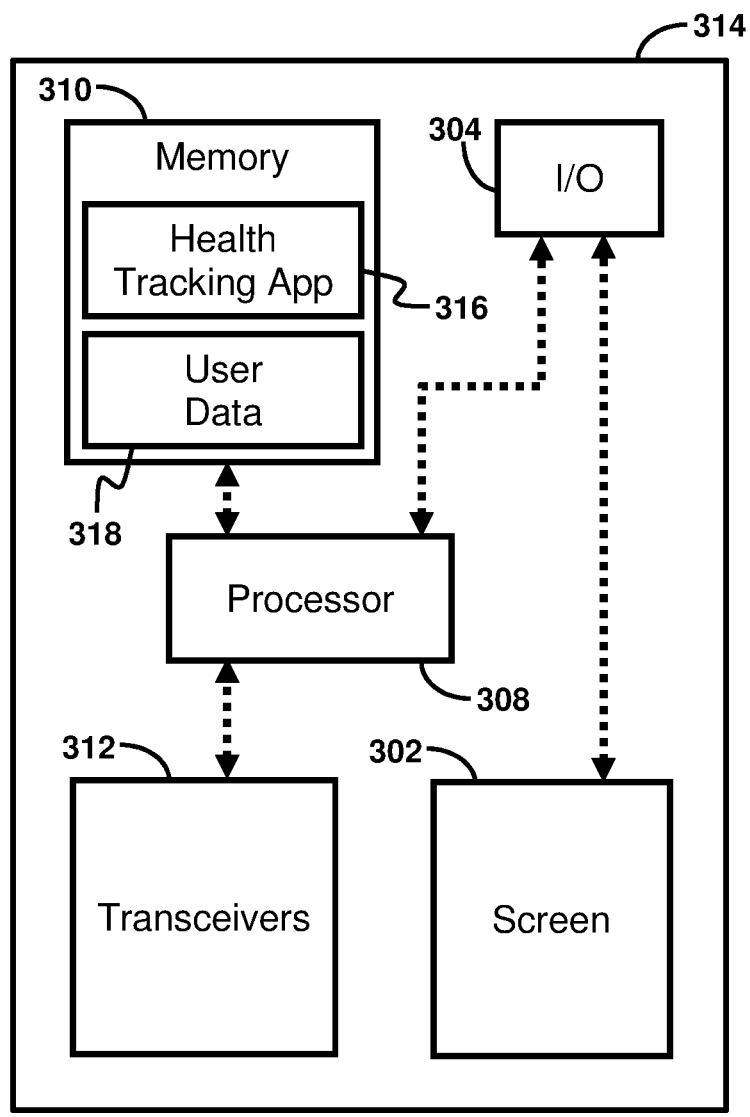
FIG. 3 shows a smart phone of the health tracking system.

With reference now to FIG. 3, in at least one embodiment the health tracking device 110 is provided in the form of a smartphone 110A. The smartphone 110A includes a display screen 302, an input/output (I/O) interface 304, a processor 308, a memory 310, and one or more transceivers 312. The smartphone 110A also includes a protective outer shell or housing 414 designed to retain and protect the electronic components positioned within the housing 414. The smartphone 110A also includes a battery (not shown) configured to power the display screen 302, processor 308, transceivers 312 and various other the electronic components within the smartphone 110A.

The display screen 302 of the smartphone 110A may be an LED screen or any of various other screens appropriate for the personal electronic device. The I/O interface 304 of the smartphone 110A includes software and hardware configured to facilitate communications with the user. The I/O interface 304 is in communication with the display screen 302 and is configured to visually display graphics, text, and other data to the user via the display screen 302. As will be recognized by those of ordinary skill in the art, the components of the health tracking device 110 may vary depending on the type of display device used. Alternative health tracking devices, such as the laptop 110B and the desktop 110C, may include much of the same functionality and components as the smartphone 110A shown in FIG. 3, but may not include all the same functionality or components and/or may include others not listed.

The processor 308 of the smartphone 110A may be any of various processors as will be recognized by those of ordinary skill in the art. The processor 308 is in communication with the I/O interface 304, the memory 310, and the transceivers 312, and is configured to deliver data to and receive data from each of these components. The memory 310 is configured to store information, including data and instructions for execution by the processor 308. It will be recognized by those of ordinary skill in the art that a "processor" includes any hardware system, hardware mechanism or hardware component that processes data, signals or other information. A processor may include a system with a central processing unit, multiple processing units, dedicated circuitry for achieving functionality, or other systems.

The transceivers 312 may be any of various devices configured for communication with other electronic devices, including the ability to send communication signals and receive communication signals. The transceivers 312 may include different types of transceivers configured to communicate with different networks and systems. Such transceivers are well known and will be recognized by those of ordinary skill in the art.

In some embodiments, the transceivers 312 include at least one transceiver configured to allow the smartphone 110A to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceivers 312 include at least one transceiver configured to allow the smartphone 110A to communicate with any of various local area networks using Wi-Fi, Bluetooth® or any of various other communications schemes.

In some embodiments, the memory 310 includes program instructions for a graphical user interface configured to provide a client-side health tracking application 316. The memory 310 may further be configured to store certain user data 318, such as e.g., user gender, height, weight, user identifier, password, etc. Additionally, health related data (e.g., data collected from one or more sensors and/or manually entered) may be stored. The processor 308 is configured to read the program instructions from the memory 310 and execute the program instructions to provide the health tracking application 316 to the user so for the purpose of performing health and fitness related tasks for the user, including displaying, modifying, and analyzing the user data 318.

In at least one embodiment, the user data 318 includes a plurality of consumable records which serves as a log of consumables that have been consumed by the user for the purpose of caloric and nutritional tracking. That is to say, the client-side health tracking application 316 is configured to display consumable records and enable the user to select consumable records (from a plurality of records accessed via the network 120), those items that correspond to consumables that he or she has consumed are stored at the client-side for the purpose of logging the consumables in this embodiment. In another alternative, such log may be stored remote from the device and/or only kept at the device for a transitory period.

The memory 310 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client side health tracking program 316) may be downloaded from a network location, such as via the Internet.

Deep Multi-Modal Pairwise Ranking Model

As discussed above, the health tracking application 218 includes a deep multi-modal pairwise ranking model 230 configured to rank consumable records for the purpose of search and recommendation features of the health tracking application 218. The deep multi-modal pairwise ranking model 230 utilizes at least one machine learning model, in particular a deep learning model, to perform pairwise ranking of candidate consumable records. As used herein, the term "machine learning model" refers to a system or set of program instructions configured to implement an algorithm or mathematical model that predicts and provides a desired output based on a given input. A machine learning model is not explicitly programmed or designed to follow particular rules in order to provide the desired output for a given input. Instead, the machine learning model is provided with a corpus of training data from which identifies or "learns" patterns and statistical relationships or structures in the data, which are generalized to make predictions with respect to new data inputs. In the case of supervised machine learning, training data is labeled as inputs and outputs and the machine learning model is trained to predict outputs for new data based on the patterns and other relationships or structures identified in the training data.

The consumable records database 224 presents unique challenges with respect to providing relevant search results and the deep multi-modal pairwise ranking model 230 is adapted to the unique nature of consumable records database 224 in order to provide more relevant search results than would be produced using traditional search and ranking mechanisms. Particularly, in many embodiments, the consumable records database 224 may include hundreds of millions of consumable records 224. As discussed above, many, if not all, of consumable records 224 are created by users of the health tracking system 100 and/or have fields that are editable by users, without the need for special authorization or privileges. Due to the crowdsourced nature of the database 224, it is likely to include many duplicative records and many records having inaccurate nutritional content information. Naturally, a crucial component for unlocking such a large but noisy database is the robust ability to search it for relevant results.

In at least one embodiment, a user inputs a text string and gets back a list of relevant consumable records from the database of consumable records 224. One natural problem that arises during the search is how to retrieve and present the most relevant consumable records 224 given the text string entered by the user. As an example, if a user inputs "orange" as the query, the result set will contain a wide range of food entities, including fruits, juices, and desserts, each with different nutritional information. As discussed above, each consumable record 224 at least includes fields for a name for the consumable item and nutritional information. However, food names are generally short in length, and the presence or absence of a single word, or differences in the word ordering in a given food name can significantly distort its semantics, which limits the effectiveness of searches performed only on the basis of the food names of the consumable records 224.

To illustrate some of the challenges in searching and ranking of records in the consumable records database 224, some examples are provided. In a first example, a user searches "apple" and records having the names "Fuji apple" and "apple pie" are returned as results. Although both results include the word "apple," the "Fuji apple" is intuitively more semantically relevant than "apple pie" based on typical search behaviors (i.e. users would generally include the word "pie" if they intended to find the dessert rather than the fruit). In a second example, a user searches "spaghetti" and records having the names "spaghetti with meat sauce" and "spaghetti sauce with meat" are returned as results. Although both results actually include the same words, "spaghetti with meat sauce" is intuitively more semantically relevant than "spaghetti sauce with meat" based on typical search behaviors (i.e. users would generally include the word "sauce" if they intended to find the sauce rather than the entrée). Additionally, it should be noted that in both examples, the nutritional contents can provide an important contextual clue to make the correct prediction. For instance, for the query="apple", the foods "Fuji apple" and "apple pie" are similar in name, but very different in nutritional contents (0.5 and 2.37 calories per 1 gram, respectively).

Given these observations, to overcome the complexities of food naming conventions in text, the deep multi-modal pairwise ranking model 230 is configured to rank candidate records in a multi-modal manner that takes into account both the food name and the nutritional contents of the candidate records. Furthermore, the deep multi-modal pairwise ranking model 230 utilizes machine learning to adapt to real behavior of users of the health tracking system 100.

Figure 4:
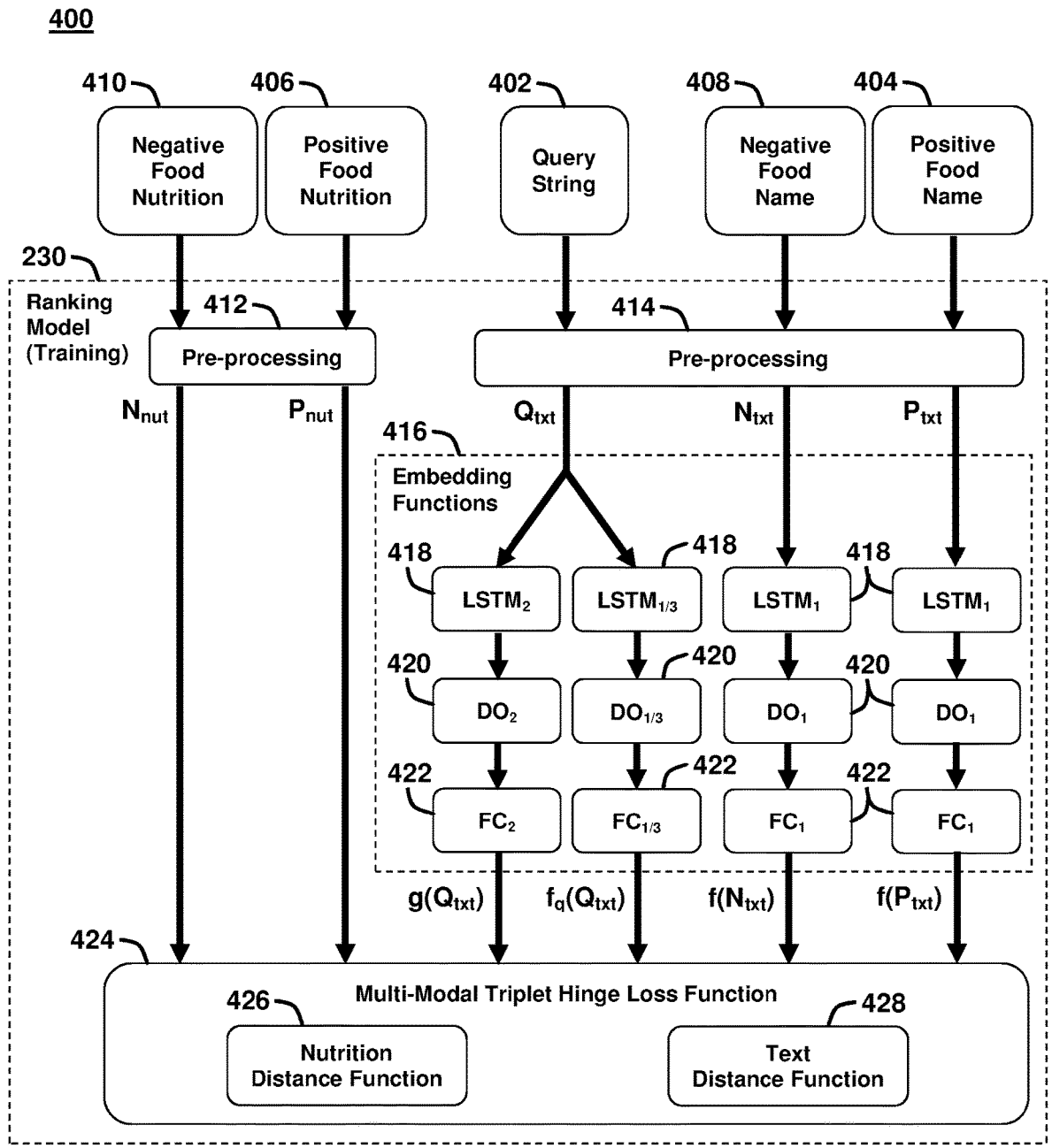
FIG. 4 shows an exemplary embodiment of a training process of a deep multi-modal pairwise ranking model.

FIG. 4 illustrates an exemplary embodiment of a training process 400 of the deep multi-modal pairwise ranking model 230. The multi-modal pairwise ranking model 230 includes a system or set of program instructions configured to implement the training process 400. During the training process 400, the ranking model 230 is provided with a plurality of training triplet inputs for training. Each training triplet input comprises (1) a query string (Q) 402, (2) a positive candidate food (P) having a name 404 and nutrition 406, and (3) negative candidate food (N) having a name 408 and nutrition 410. In each triplet input, the query string (Q) 402 is an exemplary search term, the positive candidate food (P) is a relevant food, and the negative candidate food (N) is an irrelevant food (e.g., for a query string "orange," a "large orange" may be the relevant consumable and an "orange soda" may be the irrelevant consumable). In some embodiments, the plurality of training triplet inputs are generated based on historical data detailing search terms previously used by users of the health tracking system 100, previous search results thereof, and which of the search results were most frequently selected by the users that used the search term.

In a pre-processing operation 412 of the deep multi-modal pairwise ranking model 230, the positive food candidate nutrition 406 and the negative food candidate nutrition 410 are converted into normalized n-length real-valued vectors $P_{nut}$ and $N_{nut}$, respectively. In at least one embodiment, a 4×1 macro-nutrient vector [e; $f$; c; p] is extracted from each of the positive and negative nutrition information 406 and 410, where e is a total energy content, $f$ is a total grams of fat, c is a total grams of carbohydrates, and p is a total grams of protein. In at least one embodiment, the macro-nutrient vector [e; $f$; c; p] is normalized on a per-unit-mass basis, a per-unit-weight basis, or a per-unit-volume basis (e.g., per gram, per pound, per milliliter, etc.) during the pre-processing operation 412.

In a preprocessing 414 of the deep multi-modal pairwise ranking model 230, the query string (Q) 402, the positive food candidate name 404, and the negative food candidate name 408 are converted into numeric matrices $Q_{txt}$, $P_{txt}$, and $N_{txt}$, respectively. In one embodiment, the ranking model 230 builds or receives a dictionary of all words appearing in the training data (i.e. the training triplet inputs), which may for example contain 10K distinct words, after applying some standard string normalization operations. For each of the text inputs 402, 404, and 408, each word is represented as a one-hot vector of length equal to the number of distinct words in the dictionary (e.g., a 1×10K vector), wherein the index value of the given word has the value 1 and each other index has the value 0. For the sake of convenience, the number of words per food name or query string may be limited to a predetermined number (e.g., 5 words) and longer and shorter texts are truncated or zero-padded, respectively. The one-hot vectors for the words of the respective text inputs 402, 404, and 408 are combined to form the numeric matrices $Q_{txt}$, $P_{txt}$, and $N_{txt}$, each being, for example, a matrix of size 5×10K.

During the training process 400 of the ranking model 230, the numeric matrices $Q_{txt}$, $P_{txt}$, and $N_{txt}$ are provided to embedding functions 416. The embedding functions 416 comprise a plurality of unknown functions which are learned during the training process 400 based on the plurality of training triplet inputs. In the embodiment shown, the unknown functions to be learned include the embedding functions $f(.)$, $f_q(.)$, and $g(.)$. The embedding functions $f_q(.)$ and $f(.)$ are text embedding functions configured to receive the numeric matrix $Q_{txt}$, and the numeric matrices $P_{txt}$ and $N_{txt}$, respectively, and to transform the input matrices into respective m-dimensional feature vectors in a learned text feature space (i.e. $f_q(Q_{txt})$, $f(P_{txt})$ and $f(N_{txt}) \in \mathbb{R}^m$). In some embodiments, the query text embedding function $f_q(.)$ may be different from the food name text embedding function $f(.)$, but in at least one embodiment, they are set to be identical (i.e., query string and food names are assumed to have the same language model). In contrast, the embedding function $g(.)$ is a query text nutrition embedding function configured to receive the numeric matrix $Q_{txt}$ and to transform the input matrix into an n-dimensional normalized nutrition vector in a learned nutritional content space (i.e. $g(Q_{txt}) \in \mathbb{R}^n$), essentially analogous to the nutrition vectors $P_{nut}$ and $N_{nut}$. In some embodiments, the embedding functions 416 may include additional unknown embedding functions for incorporating additional modalities, such as images of consumables that might be stored in the consumable records 224.

Each of the embedding functions $f(.)$, $f_q(.)$, and $g(.)$ are implemented by an Long Short Term Memory (LSTM) layer 418, a dropout (DO) layer 420, and a fully connected (FC) layer 422. Particularly, the food name text embedding function $f(.)$ is implemented by $LSTM_1$, $DO_1$, and $FC_1$. The query nutrition embedding function $g(.)$ is implemented by $LSTM_2$, $DO_2$, and $FC_2$. The query text embedding function $f_q(.)$, is implemented by $LSTM_3$, $DO_3$, and $FC_3$ (alternatively, by $LSTM_1$, $DO_1$, and $FC_1$ in the case that $f(.)$ and $f_q(.)$ are chosen to be identical to one another).

In some embodiments, the text embedding functions $f(.)$ and $f_q(.)$, which receive numeric matrices corresponding to the positive candidate food names ($P_{txt}$), negative candidate food names ($N_{txt}$), and query strings ($Q_{txt}$), are configured to generate feature vectors of size m=10. In one embodiment, the LSTM layers 418 are configured with 40 dimensions and the FC layers 422 are configured to reduce their outputs to 1×m (e.g. 1×10) vectors. Both positive and negative food name instances of the LSTM layer 418 ($LSTM_1$) and the FC layer 422 ($FC_1$) share the same parameter values since these should be equally embedded and learned in the model. As discussed above, in some embodiments embedding functions $f(.)$ and $f_q(.)$ are set to be identical. In such embodiments, the same parameters are used in the LSTM layer 418 ($LSTM_1$) and the FC layer 422 ($FC_1$) for all three text inputs, $Q_{txt}$, $P_{txt}$ and $N_{txt}$. However, in some embodiments, a separate LSTM layer 418 ($LSTM_3$) and separate FC layer 422 ($FC_3$) having separate parameter values may be used is used for query text strings $Q_{txt}$.

In some embodiments, query text nutrition embedding function $g(.)$, which receives numeric matrices corresponding to query text strings ($Q_{txt}$), is configured to generate normalized nutrition vectors of size n=4 (e.g. 1×4), to be comparable with the other nutrition vectors $P_{nut}$ and $N_{nut}$. In one embodiment, the LSTM layer 418 is configured with 40 dimensions and the FC layer 422 is configured to reduce the outputs to 1×n (e.g. 1×4) vectors. The LSTM layer 418 ($LSTM_2$) and the FC layer 422 ($FC_2$) of the query text nutrition embedding function $g(.)$ are kept wholly apart from those of the text embedding functions $f(.)$ and $f_q(.)$, with different parameter values because similarity in names does not imply similarity in nutrition, and vice versa.

In some embodiments, in order to prevent overfitting to the training data, all intermediate vectors are passed through dropout layers 420 (e.g., with a p value=0.5) before being fed into the FC layers 422. Overfitting on the training data means that the model learns to perform well on the training data but fails to generalize when making predictions on new data. The dropout layers 420 are configured to randomly mask network units during training of the model 230, which reduces overfitting to the training data. This helps to improve the generalization ability of the trained model in making predictions on new data not seen during the training process.

During the training process 400 of the ranking model 230, the vector outputs of the embedding functions 416 (i.e. $f_q(Q_{txt})$, $f(Q_{txt})$, $f(O_{txt})$ and $f(N_{txt})$) and the vector outputs of the pre-processing 412 (i.e. $P_{nut}$ and $N_{nut}$) are provided to a multi-modal triplet hinge loss function 424. The multi-modal triplet hinge loss function 424 is advantageously configured to take multiple modalities (i.e. food name text and food nutritional content) into account, while preserving the individual geometric properties of each modality. Particularly, the multi-modal triplet hinge loss function 424 incorporates a distinct distance function for each modality to preserve the individual geometric properties. This is in contrast to, for example, simply concatenating the input vectors and using a single distance function, which would distort the individual geometric properties of the input vectors In one embodiment, the multi-modal triplet hinge loss function 424 includes a nutrition distance function 426 configured to determine a distance between two nutritional content vectors, and a text distance function 428 configured to determine a distance between two text feature vectors. In some embodiments, the multi-modal triplet hinge loss function 424 may include additional distance functions for incorporating additional modalities, such as images of consumables that might be stored in the consumable records 224. During the training process 400, the multi-modal triplet hinge loss function 424 and the distance functions 426 and 428 thereof are used to adjust parameter values for the LSTM layers 418 and/or the FC layers 422 such that input text strings having similar meanings are transformed into similar feature vectors.

The nutrition distance function 426 may comprise any function or operation configured to determine a distance between two nutritional content vectors. However, in at least one embodiment, the exemplary nutrition distance function 426 described below is used. As discussed above, a 4×1 macro-nutrient vector [e; f; c; p] can be extracted from any candidate consumable record, where e is a total energy content, f is a total grams of fat, c is a total grams of carbohydrates, and p is a total grams of protein This vector satisfies the constraint of $e=9\times f+4\times c+4\times p$. Hence, the contribution of each macro-nutrient towards the total energy can be measured by:

$$f' = \frac{9\times f}{e}, c' = \frac{4\times c}{e}, p' = \frac{4\times p}{e},$$

hence $f'+c'+p'=1$. Any nutritional content vector [e; $f$; c; p] can be decomposed into two components: (1) a total energy e, and (2) a normalized vector of macro-nutrients [$f'$; c'; p']. Note that total energy e is a positive value, i.e. $e\in \mathbb{R}^+$ while the square root density vector, i.e. $M=[\sqrt{f'}, \sqrt{c'}, \sqrt{p'}]$, belongs to two-dimensional sphere $\mathbb{S}^2$, since $\Sigma_{i=1}^{3} M_i^2 = 1$. Thus, any nutritional content vector [e; $f$; c; p], can be parameterized as $[e]\times[\sqrt{f'}, \sqrt{c'}, \sqrt{p'}]$, belonging to the $\mathbb{R}^+\times\mathbb{S}^2$ product space. Given two nutritional content vectors $N_1=[e_1; f_1; c_1; p_1]$ and $N_2=[e_2; f_2; c_2; p_2]$, an intrinsic distance function on this product space can be computed as $dist_{nut}^2(N_1, N_2) = dist_{\mathbb{R}+}^2(e_1, e_2) + dist_{\mathbb{S}^2}^2(M_1, M_2)$, where $$M_i = \left[\sqrt{\frac{9\times f_i}{e_i}}, \sqrt{\frac{4\times c_i}{e_i}}, \sqrt{\frac{4\times p_i}{e_i}}\right]$$

and i=1, 2. The second term corresponds to the intrinsic distance function on sphere which is computed as $dist_{\mathbb{S}^2} = \cos^{-1}(<M_1, M_2>)$, where $<.>$ is the vector inner product operator. Note that $\mathbb{R}^+$ is equivalent to the space of 1×1 Symmetric Positive Definite (SPD) matrices. Thus, its intrinsic distance is defined as $$dist_{\mathbb{R}+}^2(e_1, e_2) = \left(\text{Log}\left(\frac{e_1}{e_2}\right)\right)^2.$$

in summary, given $N_i$, $M_i$ and $e_i$ defined as above, we have the following equation for determining the distance between two nutrient vectors $N_1$ and $N_2$:

$$dist_{nut}^2(N_1, N_2) = [\cos^{-1}(<M_1, M_2>)]^2 + \left[\text{Log}\left(\frac{e_1}{e_2}\right)\right]^2. \quad (1)$$

The text distance function 428 may comprise any function or operation configured to determine a distance between two text feature vectors. In some embodiments, Euclidean (L2) distance or Manhattan (L1) distance is used. Particularly, in one embodiment, the Euclidean distance formula is used to determine the distance between two text feature vectors $T_1$ and $T_2$:

$$dist_{txt}(T_1, T_2) = \sqrt{\|T_2 - T_1\|^2} \quad (2).$$

The multi-modal triplet hinge loss function 424 is used for training or "learning" the unknown embedding functions $f(.)$, $f_q(.)$, and $g(.)$. Particularly, the output of the multi-modal triplet hinge loss function 424 is used to adjust parameter values for the LSTM layers 418 and/or the FC layers 422 such that input text strings having similar meanings are transformed into similar feature vectors. Advantageously, using the distance functions 426 and 428 (e.g., as represented by the equations (1) and (2)) the multi-modal triplet hinge loss function 424 take multiple modalities (i.e. food name text and food nutritional content) into account, while preserving the individual geometric properties of each modality. As discussed above, the text embedding functions $f_q(.)$ and $f(.)$ are configured to transform the input matrices into respective m-dimensional feature vectors (i.e. $f_q(Q_{txt})$, $f(P_{txt})$ and $f(N_{txt}) \in \mathbb{R}^m$). In contrast, the query nutrition embedding function $g(.)$ is configured to transform the input matrix into an n-dimensional normalized nutrition vector (i.e. $g(Q_{txt}) \in \mathbb{R}^n$). Additionally, the nutrition vectors $P_{nut}$ and $N_{nut}$ are naturally in this embedded space of $\mathbb{R}^n$. Formally, pair-wise multi-modal ranking can now be formulated by using the following three text and nutrition vector pairs: $(f_q(Q_{txt}), g(Q_{txt}))$, $(f(P_{txt}), P_{nut})$, and $(f(N_{txt}), N_{nut})$. As discussed above, the nutrition vectors belong to the product space of $\mathbb{S}^+\times\mathbb{S}^2$. Hence, each pair $(T_i, N_i)$ is a vector in the product space, $\mathbb{R}^m + \mathbb{R}^+\times\mathbb{S}^2$. Accordingly, the distance function for determining a distance between two text and nutrition vector pairs $(T_1, N_1)$ and $(T_2, N_2)$ in this product space may be defined as:

$$dist^2((T_1, N_1), (T_2, N_2)) = dist_{txt}^2(T_1, T_2) + dist_{nut}^2(N_1, N_2) \quad (3),$$

where $dist_{txt}$ and $dist_{nut}$ correspond to the distance functions defined above in equations (1) and (2), respectively.

Note that the linearity of the distance equation (3) allows that the distance function can be decomposed into text-based component and nutrition-based component. In this way, the food name and nutrition modalities are taken into account while preserving their individual geometric. Furthermore, in embodiments having additional or alternative modalities (e.g., images as mentioned above), the equation (3) is easily modified to incorporate the additional modality. Using the distance equation (3) on the product space $\mathbb{R}^m \times \mathbb{R}^+ \times \mathbb{S}^2$, the multi-modal triplet hinge loss function 424 for determining a hinge loss based on the inputs $(Q_{txt}, P_{txt}, N_{txt}, P_{nut}, N_{nut})$ can be defined as:

$$L(Q_{txt}, P_{txt}, N_{txt}, P_{nut}, N_{nut}) = \max\{0, \gamma + [dist_{txt}^2(f_q(Q_{txt}), f(P_{txt})) + dist_{nut}^2(g(Q_{txt}), P_{nut})] - [dist_{txt}^2(f_q(Q_{txt}), f(N_{txt})) + dist_{nut}^2(g(Q_{txt}), N_{nut})]\} \quad (4),$$

where $\gamma$ is a gap parameter which governs a separation level between positive and negative instances. During the training process 400, parameter values of the embedding functions $f_q(.)$, $f(.)$, and $g(.)$ are adjusted or "learned" based on the hinge loss L. In some embodiments, the deep multi-modal pairwise ranking model 230 may comprise as many as 3M unknown parameters which are learned using the training triplet inputs.

FIG. 5 shows a method 500 of operating the health tracking system 100 to train the deep multi-modal pairwise ranking model 230. In the description of the method, statements that the method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A above may be such a controller or processor. Alternatively, the controller may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

The method 500 begins with a step of receiving a plurality of training inputs, each training input including (i) a query string, (ii) a first descriptive string and first nutritional data labeled as corresponding to a correct output, and (iii) a second descriptive string and second nutritional data labeled as corresponding to an incorrect output (block 510). Particularly, with respect to the embodiments described in detail herein, the processing circuitry/logic 204 of the server 200 is configured to receive a plurality of training triplet inputs <Q, P, N>, as discussed above with respect to FIG. 4, where Q is a query string, P is a positive food candidate having a food name and nutritional information, and N is a negative food candidate having a food name and nutritional information. The positive food candidate P is considered relevant to the query string Q or, in other words, is a correct output for the deep multi-modal pairwise ranking model 230. The negative food candidate N is considered irrelevant to the query string Q or, in other words, an incorrect output for the model 230.

In at least one embodiment, training triplet inputs <Q, P, N> are generated and/or collected using randomly sampled food search logs, which are stored in the memory 206 (e.g., the operational records 226) and produced by past search activities of users of the health tracking system 100. In one embodiment, the processing circuitry/logic 204 of the server 200 is configured to randomly select a set of past queries Q from the food search logs and retrieve a subset of consumable records 224 and/or food names thereof that have frequently appeared within the top search results (e.g., top 5) for those queries Q, based on the food search logs. Next, the processing circuitry/logic 204 is configured to compute a Click-Through Ratio (CTR)r(F|Q), for each food F and corresponding query Q, based on previous selections of user searching the query Q. Next, the processing circuitry/logic 204 is configured to label each pair (Q, F) positive if r(F|Q)> e.g. 0.2, or negative if r(F|Q)<e.g. 0.05. Additionally, the processing circuitry/logic 204 is configured to retrieve corresponding nutritional content for all candidates. For each query Q, the processing circuitry/logic 204 is configured to generate at least one training triplet input in the form of <Q, P, N>. In one embodiment, as many as 6.5M randomly selected training triplet inputs are produced using the food search logs.

The method 500 continues with a step of, for each training input, generating (i) a first feature vector based on the first descriptive string, (ii) a second feature vector based on the second descriptive string, and (iii) a third feature vector based on the query string, using at least one first embedding function of a machine learning model (block 520). Particularly, the processing circuitry/logic 204 of the server 200 is configured to generate the numeric matrices $Q_{txt}$, $P_{txt}$, and $N_{txt}$ based on the query Q, the food name of the positive candidate P, and the food name of the negative candidate N, as discussed above with respect to the preprocessing operation 414 of FIG. 4. Next, the processing circuitry/logic 204 is configured to generate the feature vectors $f_q(Q_{txt})$, $f(P_{txt})$, and $f(N_{txt})$, using the embedding functions $f_q(.)$ and $f(.)$ of the deep multi-modal pairwise ranking model 230, as discussed above in greater detail with respect to the embedding functions 416 of FIG. 4. As discussed above, in at least some embodiments embedding functions $f_q(.)$ and $f(.)$ are set to be identical to one another.

The method 500 continues with a step of, for each training input, generating (i) a first nutrition information vector from the first nutritional data and (ii) a second nutrition information vector from the second nutritional data (block 530). Particularly, the processing circuitry/logic 204 is configured to form the nutrition vectors $P_{nut}$ and $N_{nut}$ based on the nutrition contents of the positive candidate P and the nutrition contents of the negative candidate N, as discussed above with respect to the preprocessing operations 412 of FIG. 4. In one embodiment, the processing circuitry/logic 204 is configured to normalize the vectors $P_{nut}$ and $N_{nut}$ on a per-unit-mass basis, a per-unit-weight basis, or a per-unit-volume basis (e.g., per gram, per pound, per milliliter, etc.).

The method 500 continues with a step of, for each training input, generating a third nutrition information vector based on the query string, using a second embedding function of the machine learning model (block 540). Particularly, the processing circuitry/logic 204 of the server 200 is configured to generate the normalized nutrition vector $g(Q_{txt})$ using the embedding function $g(.)$ of the deep multi-modal pairwise ranking model 230, as discussed above in greater detail with respect to the embedding functions 416 of FIG. 4.

The method 500 continues with a step of, for each training input, determining a hinge loss based on the first feature vector, the second feature vector, the third feature vector, first nutrition information vector, the second nutrition information vector, and the third nutrition information vector (block 550). Particularly, the processing circuitry/logic 204 is configured to determine a first distance $dist_{txt}(f_q(Q_{txt}), f(P_{txt}))$ between the feature vector $f_q(Q_{txt})$ and the feature vector $f(P_{txt})$ (e.g., using the equation (2), above). Additionally, the processing circuitry/logic 204 is configured to determine a second distance $dist_{nut}(g(Q_{txt}), P_{nut})$ between the nutrition vector $g(Q_{txt})$ and the nutrition vector $P_{nut}$ (e.g., using the equation (1), discussed above). The processing circuitry/logic 204 is configured to determine a square of a first total distance $dist^2((f_q(Q_{txt}), g(Q_{txt})), (f(P_{txt}), P_{nut}))$ as a sum of a square of the first distance and a square of the second distance (e.g., using the equation (3), discussed above), which represents a total distance from the positive food candidate P to the query Q or, in other words, the model's predicted relevance of the positive food candidate P to the query Q.

Next, the processing circuitry/logic 204 is configured to determine a third distance $dist_{txt}(f_q(Q_{txt}), f(N_{txt}))$ between the feature vector $f_q(Q_{txt})$ and the feature vector $f(N_{txt})$ (e.g., using the equation (2), above). Additionally, the processing circuitry/logic 204 is configured to determine a fourth distance $dist_{nut}(g(Q_{txt}), N_{nut})$ between the nutrition vector $g(Q_{txt})$ and the nutrition vector $N_{nut}$ (e.g., using the equation (1), discussed above). The processing circuitry/logic 204 is configured to determine a square of a second total distance $dist^2((f_q(Q_{txt}), g(Q_{txt})), (f(N_{txt}), N_{nut}))$ as a sum of a square of the third distance and a square of the fourth distance (e.g., using the equation (3), discussed above), which represents a total distance from the negative food candidate N to the query Q or, in other words, the model's predicted relevance of the negative food candidate N to the query Q.

Finally, the processing circuitry/logic 204 is configured to determine a hinge loss L as the maximum of (i) zero and (ii) a difference between the square of the first total distance and the square of the second total distance, plus a gap parameter which governs a separation level between positive and negative instances (e.g., using the equation (4), discussed above).

The method 500 continues with a step of, for each training input, adjusting parameter values of the at least one first embedding function and the second embedding functions based on the hinge loss (block 560). Particularly, for each training triplet input, the processing circuitry/logic 204 is configured to adjust parameter values of the deep multi-modal pairwise ranking model 230, in particular of the embedding functions $f_q(.)$, $f(.)$, and $g(.)$, based on the determined hinge loss L. In this way, the model 230 learns from the training triplet inputs. In some embodiments, the model 230 may comprise as many as 3M unknown parameters which are learned using the training triplet inputs.

Figure 6:
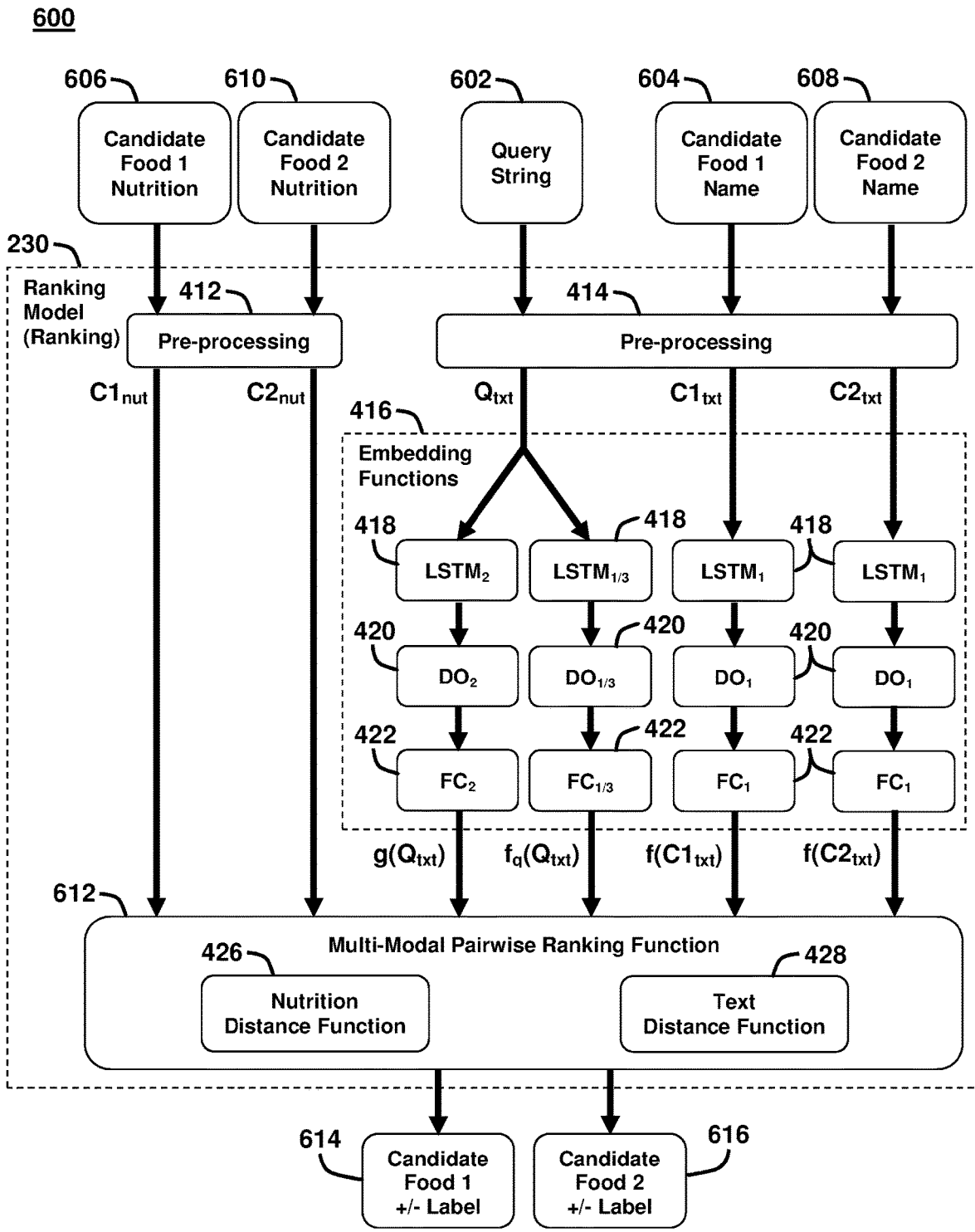
FIG. 6 shows an exemplary embodiment of a ranking process of the deep multi-modal pairwise ranking model.

FIG. 6 illustrates an exemplary embodiment of a pairwise ranking process 600 of the deep multi-modal pairwise ranking model 230. The multi-modal pairwise ranking model 230 further includes a system or set of program instructions configured to implement the pairwise ranking process 600. During the pairwise ranking process 600, the ranking model 230 is provided with a pairwise ranking triplet input. The triplet input comprises (1) a query string (Q) 602, (2) a first candidate food (C1) having a name 604 and nutrition 606, and (3) a second candidate food (C2) having a name 608 and nutrition 610. The pairwise ranking process 600 is configured to perform a pairwise ranking of the first candidate food C1 and the second candidate food C2 based on their predicted relevance to query string Q.

During the pairwise ranking process 600 of the deep multi-modal pairwise ranking model 230, the pre-processing operation 412, discussed above with respect to the training process 400, outputs nutrition vectors $C1_{nut}$ and $C2_{nut}$ based on the first and second candidate food nutrition information 606 and 610, respectively. Similarly, the pre-processing operation 414, also discussed above with respect to the training process 400, outputs numeric matrices $Q_{txt}$, $C1_{txt}$, and $C2_{txt}$ based on the query string 602, the first candidate food name 604, and the second candidate food name 608, respectively.

The numeric matrices $Q_{txt}$, $C1_{txt}$, and $C2_{txt}$ are provided to embedding functions 416, which include the embedding functions $f_q(.)$, $f(.)$, and $g(.)$, discussed above, which were learned in the training process 400. The embedding functions $f_q(.)$ and $f(.)$ transform the input matrices $Q_{txt}$, $C1_{txt}$, and $C2_{txt}$ into respective m-dimensional feature vectors in a learned text feature space (i.e. $f_q(Q_{txt})$, $f(C1_{txt})$ and $f(C2_{txt}) \in \mathbb{R}^m$). The embedding function $g(.)$ transforms the input matrix $Q_{txt}$ into an n-dimensional normalized nutrition vector in a learned nutritional content space (i.e. $g(Q_{txt}) \in \mathbb{R}^n$), essentially analogous to the nutrition vectors $C1_{nut}$ and $C2_{nut}$.

The vector outputs of the embedding functions 416 (i.e. $f_q(Q_{txt})$, $g(Q_{txt})$, $f(C1_{txt})$ and $f(C2_{txt})$) and the vector outputs of the pre-processing 412 (i.e. $C1_{nut}$ and $C2_{nut}$) are provided to a multi-modal pairwise ranking function 612. The multi-modal pairwise ranking function 612 is advantageously configured to take multiple modalities (i.e. food name text and food nutritional content) into account, while preserving the individual geometric properties of each modality.

Similar to the multi-modal triplet hinge loss function 424 discussed above, the multi-modal pairwise ranking function 612 incorporates a distinct distance function for each modality to preserve the individual geometric properties. In one embodiment, the multi-modal pairwise ranking function 612 includes the nutrition distance function 426 and the text distance function 428, discussed above. The nutrition distance function 426 may comprise any function or operation configured to determine a distance between two nutritional content vectors. However, in at least one embodiment, the nutrition distance function 426 is embodied by the equation (1) described above. Similarly, the text distance function 428 may comprise any function or operation configured to determine a distance between two text feature vectors. However, in at least one embodiment, the text distance function 428 is embodied by the equation (2) described above. In some embodiments, the multi-modal pairwise ranking function 612 may include additional distance functions for incorporating additional modalities, such as images of consumables that might be stored in the consumable records 224.

The multi-modal pairwise ranking function 612 is configured to determine which of the food candidates C1 and C2 are more relevant to the query string Q and assign a positive label to the more relevant one of candidates C1 and C2, and a negative label to the less relevant one of candidates C1 and C2. Particularly, the multi-modal pairwise ranking function 612 calculates a square of a first total distance $dist^2((f_q(Q_{txt}), g(Q_{txt})), (f(C1_{txt}), C1_{nut}))$ between the query string Q and the first food candidate C1 (e.g., using the equation (3), discussed above), which represents the model's predicted relevance of the first food candidate C1 to the query string Q. Next, the multi-modal pairwise ranking function 612 calculates a square of a second total distance $dist^2((f_q(Q_{txt}), g(Q_{txt})), (f(C2_{txt}), C2_{nut}))$ between the query Q and the second food candidate C2 (e.g., using the equation (3), discussed above), which represents the model's predicted relevance of the second food candidate C2 to the query string Q.

The multi-modal pairwise ranking function 612 compares the first total distance and the second total distance (or the squares thereof) to determine which of the food candidates C1 and C2 are more relevant to the query string Q. If the first total distance is less than the second total distance, then the first food candidate C1 is more relevant and is labeled 614 as positive, while the second food candidate C2 is labeled 616 as negative. Similarly, if the second total distance is less than the first total distance, then the second food candidate C2 is more relevant and is labeled 616 as positive, while the first food candidate C1 is labeled 614 as negative.

Figure 7:
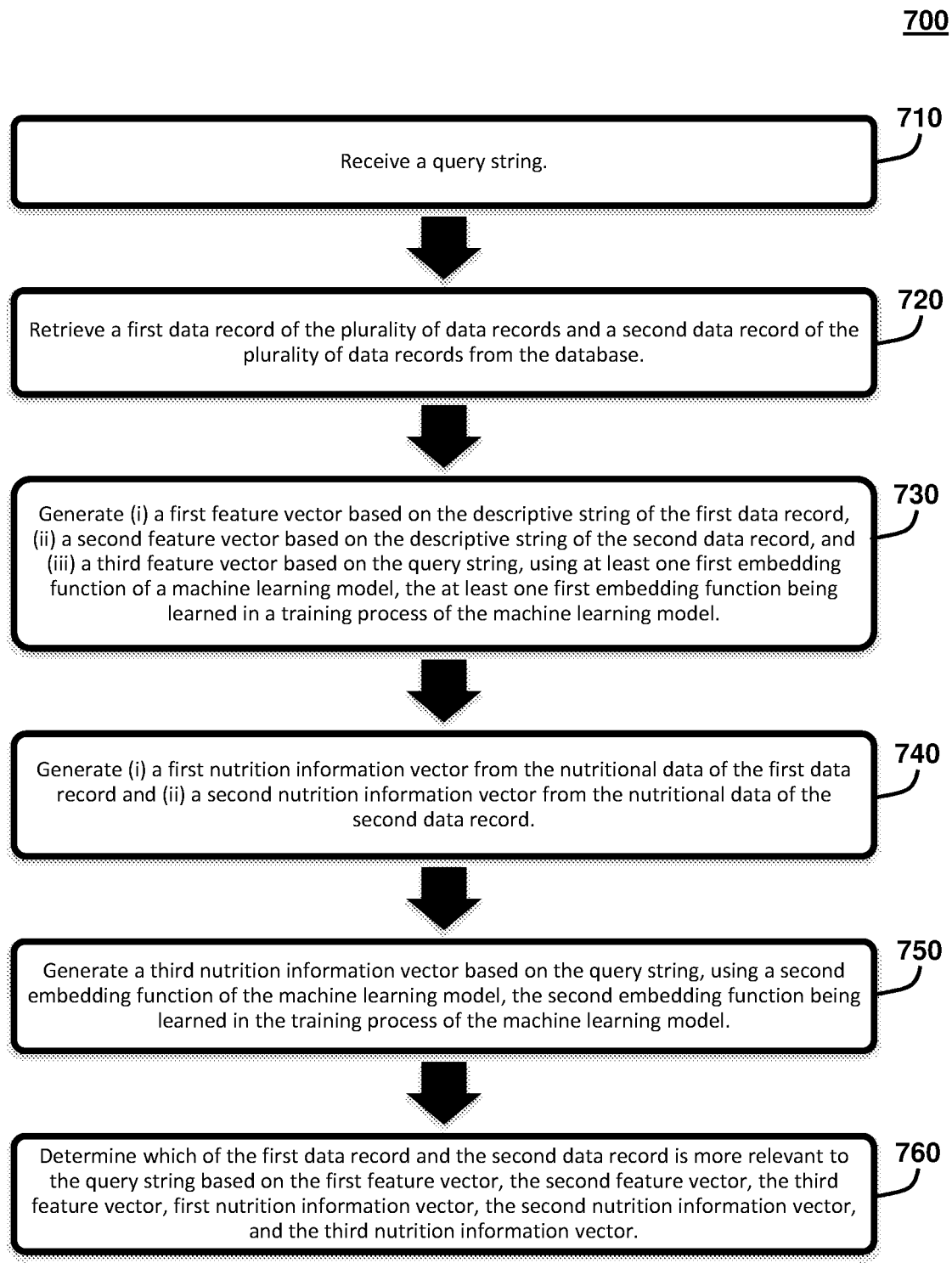
FIG. 7 shows a method of operating the health tracking system to rank a pair of consumable records using the deep multi-modal pairwise ranking model.

FIG. 7 shows a method of operating the health tracking system 100 to rank at least two consumable records using the deep multi-modal pairwise ranking model 230. In the description of the method, statements that the method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A above may be such a controller or processor. Alternatively, the controller may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

The method 700 begins with a step of receive a query string (block 710). Particularly, with respect to the embodiments described in detail herein, the processing circuitry/logic 204 of the server 200 is configured to receive a query string Q. In at least one embodiment, the processor 308 of one of the health tracking device 110 is configured to execute instructions of the client-side health tracking application 316 to enable a user to enter a search string, which will be used as the query string Q. The processor 308 is configured to operate the transceivers 312 to transmit the query string Q to the server 200. The processing circuitry/logic 204 of the server 200 is configured to operate the transceivers receive the query string Q from the health tracking device 110.

In another embodiment, the processor 308 of one of the health tracking device 110 is configured to execute instructions of the client-side health tracking application 316 to enable a user to select a consumable item with respect to which he or she would like to receive recommendations of similar consumable items. Alternatively, in some embodiments, the processor 308 of the health tracking device 110 and/or processing circuitry/logic 204 of the server 200 is configured to automatically identify a consumable item with respect to which recommendations of similar consumable items will be provided, based on one or more rules for automatically identifying the consumable item. The rules for identifying consumables items for the purpose of recommendation may include identifying frequently logged foods (i.e. foods the user likes) and identifying unhealthy foods (i.e. foods that may have healthier substitutes). The processor 308 of the health tracking device 110 and/or processing circuitry/logic 204 of the server 200 is configured to extract a food name from the consumable record 224 corresponding the selected or automatically identified consumable item, which is used as the query string Q. In some embodiments, the processor 308 is configured to operate the transceivers 312 to transmit the query string Q and/or the selected or automatically identified consumable item to the server 200. The processing circuitry/logic 204 of the server 200 is configured to operate the transceivers 214 to receive the query string Q and/or the selected or automatically identified consumable item from the health tracking device 110.

The method 700 continues with a step of retrieving a first data record of the plurality of data records and a second data record of the plurality of data records from the database (block 720). Particularly, the processing circuitry/logic 204 of the server 200 is configured to retrieve at least a first food candidate C1 and a second food candidate C2 from the consumable records database 224. In some embodiments, the processing circuitry/logic 204 is configured to retrieve a plurality of consumable records from the consumable records database 224, the plurality of consumable records including the first food candidate C1 and the second food candidate C2. Particularly, in one embodiment, the processing circuitry/logic 204 is configured to search the database 224 to generate a search results list which identifies a plurality of consumable records which may be relevant to the query string Q. In order to rank the search results list, the processing circuitry/logic 204 is configured to generate a plurality of pairwise ranking triplet inputs <Q, C1, C2>, where Q is the query string, C1 is a respective first food candidate having a food name and nutritional information, and C2 is a respective second food candidate having a food name and nutritional information.

The method 700 continues with a step of generating (i) a first feature vector based on the descriptive string of the first data record, (ii) a second feature vector based on the descriptive string of the second data record, and (iii) a third feature vector based on the query string, using at least one first embedding function of a machine learning model, the at least one first embedding function being learned in a training process of the machine learning model (block 730). Particularly, the processing circuitry/logic 204 of the server 200 is configured to generate the numeric matrices $Q_{txt}$, $C1_{txt}$ and $C2_{txt}$ based on the query Q, the food name of the first food candidate C1, and the food name of the second food candidate C2, as discussed above with respect to the preprocessing operation 414 of FIG. 6. Next, the processing circuitry/logic 204 is configured to generate the feature vectors $f_q(Q_{txt})$, $f(C1_{txt})$, and $f(C2_{txt})$, using the embedding functions $f_q(.)$ and $f(.)$ of the deep multi-modal pairwise ranking model 230, as discussed above in greater detail with respect to the embedding functions 416 of FIG. 6. As discussed above, in at least some embodiments embedding functions $f_q(.)$ and $f(.)$ are set to be identical to one another.

The method 700 continues with a step of generating (i) a first nutrition information vector from the nutritional data of the first data record and (ii) a second nutrition information vector from the nutritional data of the second data record (block 740). Particularly, the processing circuitry/logic 204 is configured to form the nutrition vectors $C1_{nut}$ and $C2_{nut}$ based on the nutrition contents of the first food candidate C1 and the nutrition contents of the second food candidate C2, as discussed above with respect to the preprocessing operations 412 of FIG. 6. In one embodiment, the processing circuitry/logic 204 is configured to normalize the vectors $C1_{nut}$ and $C27_{nut}$ on a per-unit-mass basis, a per-unit-weight basis, or a per-unit-volume basis (e.g., per gram, per pound, per milliliter, etc.).

The method 700 continues with a step of generating a third nutrition information vector based on the query string, using a second embedding function of the machine learning model, the second embedding function being learned in the training process of the machine learning model (block 750). Particularly, the processing circuitry/logic 204 of the server 200 is configured to generate the nutrition vector $g(Q_{txt})$ using the embedding function $g(.)$ of the deep multi-modal pairwise ranking model 230, as discussed above in greater detail with respect to the embedding functions 416 of FIG. 6. In one embodiment, if the embedding function $g(.)$ wasn't trained to output normalized vectors, the processing circuitry/logic 204 is configured to normalize the nutrition vector $g(Q_{txt})$ on a per-unit-mass basis, a per-unit-weight basis, or a per-unit-volume basis (e.g., per gram, per pound, per milliliter, etc.).

The method 700 continues with a step of determining which of the first data record and the second data record is more relevant to the query string based on the first feature vector, the second feature vector, the third feature vector, first nutrition information vector, the second nutrition information vector, and the third nutrition information vector (block 760). Particularly, the processing circuitry/logic 204 is configured to determine a first distance $dist_{txt}(f_q(Q_{txt}), f(C1_{txt}))$ between the feature vector $f_q(Q_{txt})$ and the feature vector $f(C1_{txt})$ (e.g., using the equation (2), above). Additionally, the processing circuitry/logic 204 is configured to determine a second distance $dist_{nut}(g(Q_{txt}), C1_{nut})$ between the nutrition vector $g(Q_{txt})$ and the nutrition vector $C1_{nut}$ (e.g., using the equation (1), discussed above). The processing circuitry/logic 204 is configured to determine a square of a first total distance $dist^2((f_q(Q_{txt}), g(Q_{txt})), (f(C1_{txt}), C1_{nut}))$ as a sum of a square of the first distance and a square of the second distance (e.g., using the equation (3), discussed above), which represents a total distance from the first food candidate C1 to the query Q or, in other words, the model's predicted relevance of the first food candidate C1 to the query Q.

Next, the processing circuitry/logic 204 is configured to determine a third distance $dist_{txt}$ ($f_q(Q_{txt})$, $f(C2_{txt})$) between the feature vector $f_q(Q_{txt})$ and the feature vector $f(C2_{txt})$ (e.g., using the equation (2), above). Additionally, the processing circuitry/logic 204 is configured to determine a fourth distance $dist_{nut}(g(Q_{txt})$, $C2_{nut})$ between the nutrition vector $g(Q_{txt})$ and the nutrition vector $C2_{nut}$ (e.g., using the equation (1), discussed above). The processing circuitry/logic 204 is configured to determine a square of a second total distance $dist^2((f_q(Q_{txt}), g(Q_{txt})), (f(C2_{txt}), C2_{nut}))$ as a sum of a square of the third distance and a square of the fourth distance (e.g., using the equation (3), discussed above), which represents a total distance from the second food candidate C2 to the query Q or, in other words, the model's predicted relevance of the second food candidate C2 to the query Q.

Finally, the processing circuitry/logic 204 is configured to compare the first total distance and the second total distance (or the squares thereof) to determine which of the food candidates C1 and C2 are more relevant to the query string Q. If the first total distance is less than the second total distance, then the first food candidate C1 is more relevant and is labeled as positive, while the second food candidate C2 is labeled as negative. Similarly, if the second total distance is less than the first total distance, then the second food candidate C2 is more relevant and is labeled as positive, while the first food candidate C1 is labeled as negative.

As discussed above, in some embodiments, a plurality of pairwise ranking triplet inputs are generated based on individual candidate consumable records in a search results list that was generated on the basis of the query string Q. In such embodiments, the processing circuitry/logic 204 is configured to repeat the steps 730-760 with respect to each of the pairwise ranking triplet inputs to perform pairwise ranking of each candidate pair C1, C2 with respect to the query string Q. Next, the processing circuitry/logic 204 is configured to generate a completely ranked search results list based on the positive and negative labels generated during the pairwise ranking of each candidate pair C1, C2. Alternatively, in some embodiments, the model 230 may be used as a kind of pointwise ranking model, in which the total distance from the query is calculated for each food candidate in search results list. The search results list is then ranked based on the relative total distances from the query for each food candidate. In some embodiments, the processing circuitry/logic 204 is configured to operate the transceivers 214 to transmit the completely ranked search results list to the appropriate health tracking device 110. The processor 308 of the health tracking device 110 is configured to present the completely ranked search results list to the user via a search results screen and/or a recommendations screen of a graphical user interface on the display screen 302.

The herein described applications utilizing the deep multi-modal pairwise ranking model 230 (e.g., the health tracking program 218 and/or health tracking application 316) improve the functioning of the processing circuitry/logic 204 and/or the processor 308, respectively or in combination by enabling it/them to provide more relevant search results by ranking candidate records in a multi-modal manner using a deep learning model that takes into account both the food name and the nutritional contents of the candidate records. Furthermore, devices that are able to train the deep learning model using historical search activities can operate more efficiently to adapt to real behavior of users of the health tracking system.

Figure 8:
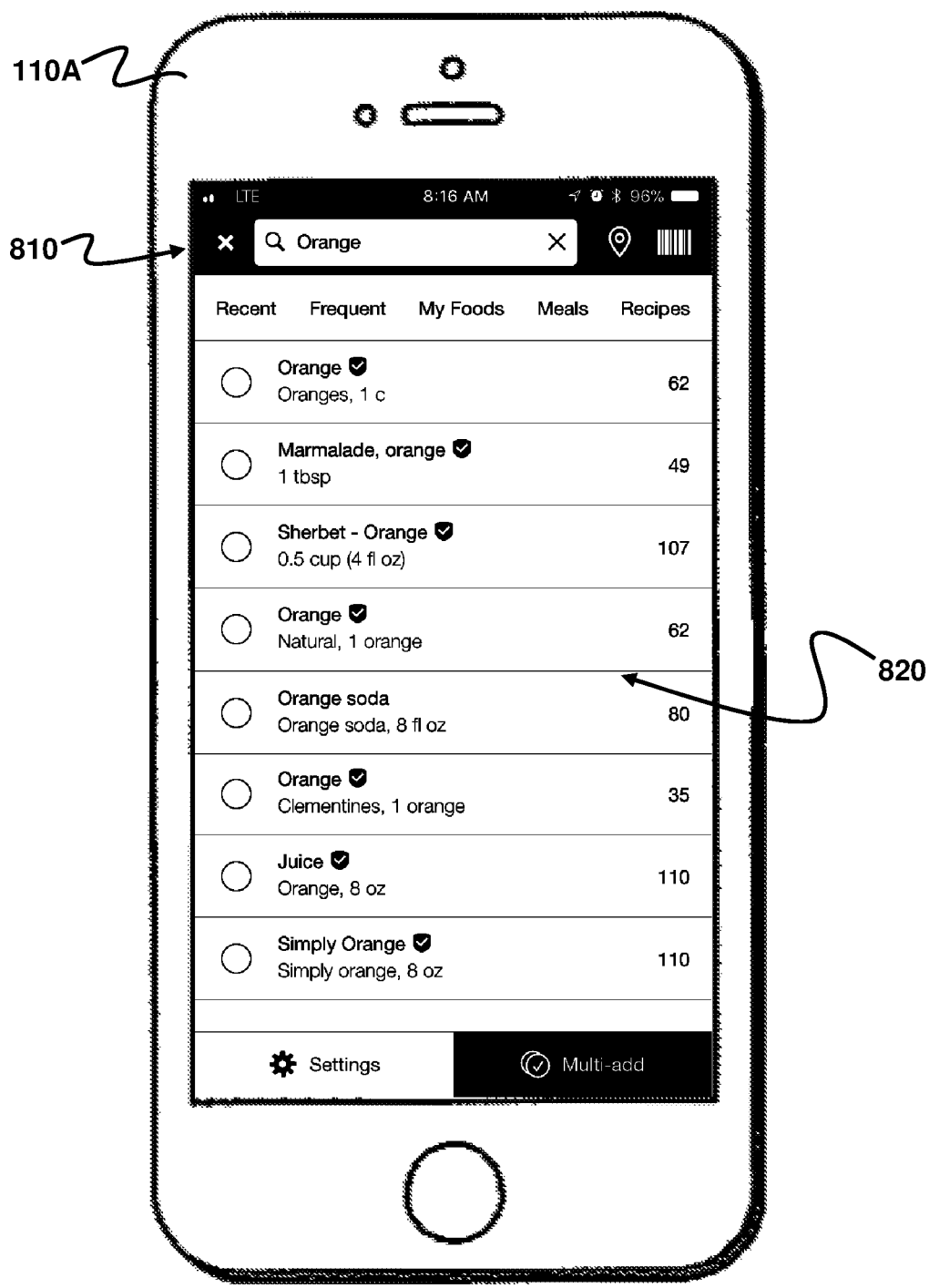
FIG. 8 shows an exemplary graphical user interface including results of a search was performed only on the basis of the food names of the consumable records.

Particularly, as discussed above, the crowdsourced and food-centric nature of the database 224 presents unique challenges with respect to providing relevant search results. Particularly, food names are generally short in length, and the presence or absence of a single word, or differences in the word ordering in a given food name can significantly distort its semantics. As a result, searches performed only on the basis of the food names of the consumable records will often yield several irrelevant results. FIG. 8 shows an exemplary graphical user interface displayed on the health tracking device 110A, in which a search of the database 224 was performed only on the basis of the food names of the consumable records. As can be seen, a user has entered the search string "orange" into a search window 810 of the graphical user interface. However, the search results 820 displayed on the graphical user interface include names for several prominently ranked consumable items that are likely irrelevant to what the user intended to find with his or her search. Particularly, given the search string "orange," the user likely wants to find the records for the fruit "Orange." However, the search results 820 also include items such as "Sherbet—Orange," "Marmalade, orange," "Orange soda," "Juice," and "Simply Orange," some of which are prominently ranked in the search results 820.

Figure 9:
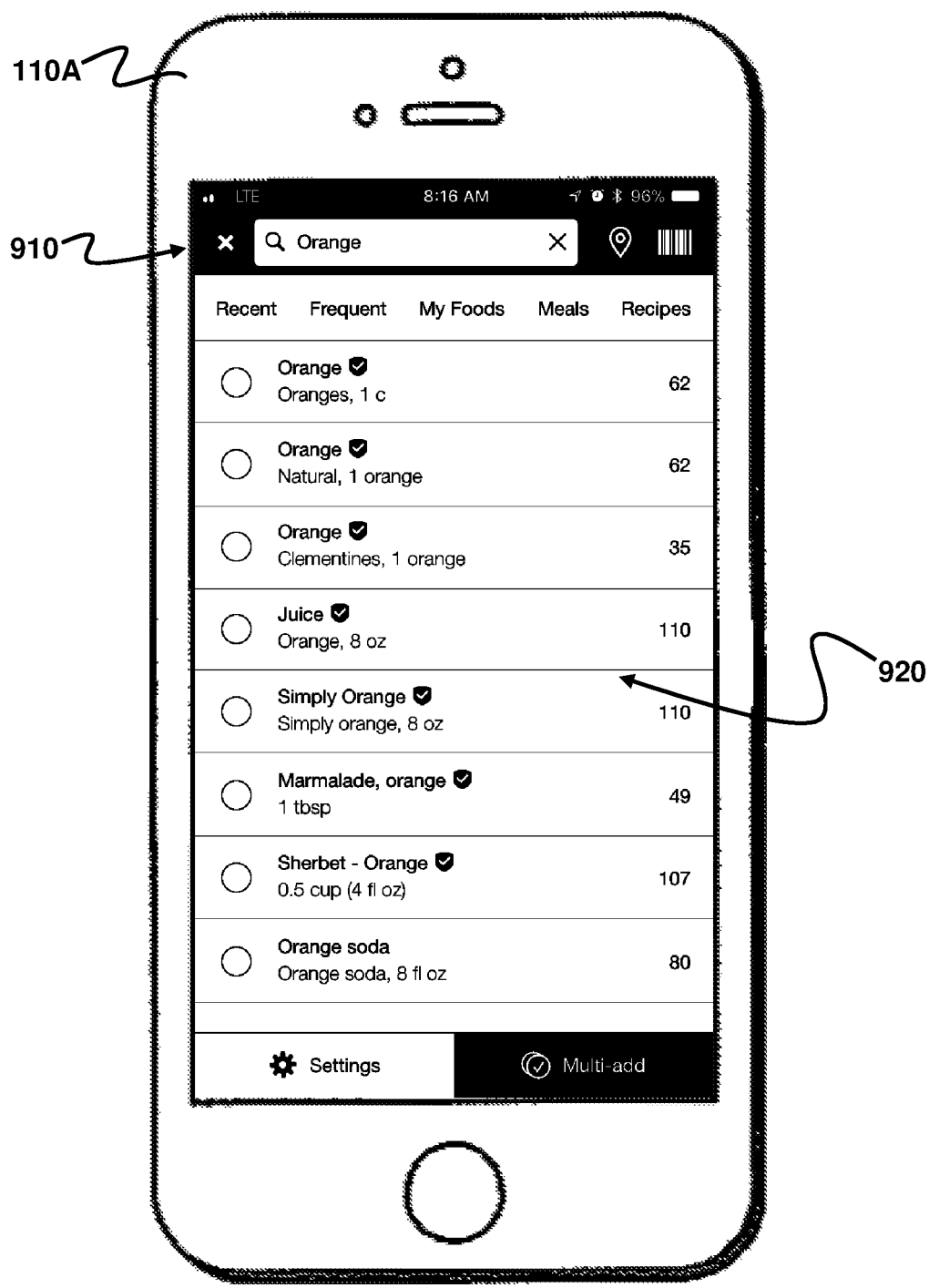
FIG. 9 shows an exemplary graphical user interface in which search results are ranked using the deep multi-modal pairwise ranking model.

The deep multi-modal pairwise ranking model 230 improves upon the search performed only on the basis of the food names of the consumable records by ranking the search results based on both the food name and the nutritional content of the corresponding consumable records. Additionally, the deep multi-modal pairwise ranking model 230 preserves the natural geometric properties of each modality by using different distance functions for text and nutrition. This is particularly advantageous when some modalities are naturally more complicated than others, e.g., nutrition vector has 4 real-value components, whereas the complexity of text data demands much larger embedding vector sizes. Furthermore, since the deep multi-modal pairwise ranking model 230 is trained using historical search activities, it advantageously adapts to real behavior of users of the health tracking system. FIG. 9 shows an exemplary graphical user interface displayed on the health tracking device 110A, in which the search results are ranked using the deep multi-modal pairwise ranking model 230. Particularly, as before, a user has entered the search string "orange" into a search window 910 of the graphical user interface. The search results 920 include the same entries as those of the search result 820, but the relevant "Orange" items are ranked prominently and the less relevant items such as "Sherbet—Orange," "Marmalade, orange," "Orange soda," "Juice," and "Simply Orange." which ranked at the bottom.

Additionally, experimental results show improved performance of the deep multi-modal pairwise ranking model 230 compared to various alternative embodiments. Particularly, the deep multi-modal pairwise ranking model 230 was compared with alternative embodiments including: (1) a Multi-Modal CNN, which is similar to the model 230, except that convolution filters with width=3 are used in place of the LSTM, (2) a Text-Based LSTM, in which only the text modality component of model 230 is used, (3) a Nutrition-Based LSTM, in which only the nutrition content modality component of model 230 is used, and (4) Multi-Modal LSTM with concatenated vectors, which is similar to the model 230, except that the embedded text and nutrition vectors are simply concatenated before calculating distances and, thus, their individual geometric properties are not preserved.

In a first test, a set of triplets consisting of a query string and two food candidates, whose labels (positive/negative) are hidden for testing were provided to the models. Each trained model assigns a positive label to one of candidates, and a negative label to other one. That accuracy of each model is compared in Table 1:

TABLE 1

| Model | Accuracy |
| --- | --- |
| Nutrition-Based LSTM | 73.04% |
| Text-Based LSTM | 82.16% |
| Multi-Modal CNN | 91.96% |
| Multi-Modal LSTM with Concatenated Vectors | 93.42% |
| The deep multi-modal pairwise ranking model 230 | 94.48% |

It is evident from the given results that the Nutrition-Based LSTM, which is solely based on nutritional content, shows the poorest performance among all five embodiments. This is due to the fact that nutrition information is not a unique identifier of foods in general, since completely different food items might have pretty similar nutrition content. Next, the Text-Based LSTM is able to reach a better accuracy, but it still falls short of the multi-modal models. This is because learning semantic relations from our crowd-sourced food database of short food names solely using text information is often insufficient as has been previously pointed out. Among multi-modal approaches, Multi-Modal CNN does a relatively good job of combining text and nutrition data to some extent. However, it is unable to achieve the same level accuracy as that of LSTM-based models. Finally, the deep multi-modal pairwise ranking model 230, in which the geometric properties of the embedded text and nutrition vectors are preserved, has the best performance, showing improvement over the Multi-Modal LSTM with Concatenated Vectors.

In a second test, distances between respective queries, "Apple" and "Black Pepper," and each corresponding candidate are measured with respect to three different models: (1) the Text-Based LSTM, (2) the Multi-Modal CNN and (3) the deep multi-modal pairwise ranking model 230. Additionally, a gap value was determined as a difference between dist(Q, N) and dist(Q, P), where dist(.) is the corresponding distance function used by each model. A positive gap value indicates that the model correctly assigned positive and negative labels to the candidates and larger positive values indicate that the model was better at distinguishing between the candidates. Conversely, a negative gap value indicates that the model incorrectly assigned positive and negative labels to the candidates and larger negative values indicate that the model was worse at distinguishing between the candidates. The performance of each model is compared in Table 2:

TABLE 2

| Query String | Positive Candidate [Nutrition Vector] | Negative Candidate [Nutrition Vector] | Model | dist(Q, P) | dist(Q, N) | Gap |
| --- | --- | --- | --- | --- | --- | --- |
| Apple | Generic Fuji Apple [0.52, 0.01, 0.14, 0.01] | Apple Strudel [2.74, 0.11, 0.42, 0.03] | Text Based LSTM | 0.657 | 0.057 | −0.600 |
| | | | Multi-Modal CNN | 0.800 | 1.004 | +0.204 |
| | | | The model 230 | 0.659 | 0.989 | +0.330 |
| Black Pepper | Spice Ground Black Pepper [2.17, 0, 0.43, 0] | Graze Black Pepper Pistachio [3.21, 0.32, 0.03, 0.10] | Text Based LSTM | 0.607 | 0.988 | +0.381 |
| | | | Multi-Modal CNN | 0.941 | 0.939 | −0.002 |
| | | | The model 230 | 0.607 | 1.172 | +0.565 |

In the first example of Table 2, "Apple", the Text-Based LSTM failed to assign the correct label to input candidates. This is because, for instance, the relative text based distance between apple and apple strudel is much smaller than text based distance between apple and generic fuji apple. In contrast, the Multi-Modal models were more successful in predicting labels, clearly showing the power of leveraging multiple modalities. The deep multi-modal pairwise ranking model 230 shows a larger separation value (i.e., gap) between two given positive and negative candidates. In the second example, "Black Pepper", labels were correctly assigned by the Text-Based LSTM, while the Multi-Modal CNN failed to do so. On the other hand, our the deep multi-modal pairwise ranking model 230 was not only able to predict the correct label, but also increased the gap between negative and positive instances by almost 20%. Both examples clearly illustrate the improved performance of the deep multi-modal pairwise ranking model 230.

Finally, in a third test, the performance in a real-world food search ranking setting was compared with respect to three different models: (1) the Text-Based LSTM, (2) the Multi-Modal CNN and (3) the deep multi-modal pairwise ranking model 230. The top 10 food search results from the top 30 most popular queries were used. Each food name was assigned a label between 0 and 5; the 0 being completely irrelevant and the 5 being completely relevant. For every food corresponding to the given query, all embedded vectors from each model were computed, and a distance between the given query and the food candidate was measured. All items were ranked in an ascending order, with respect to its distance to the given query, and finally Normalized Discounted Cumulative gain (NDCG) score was computed for each ranked set. The NDCG scores of each model is compared in Table 3:

TABLE 3

| Model | "apple" | "black pepper" | "salt" | "white flour" | "pizza" | Average over 30 queries |
|---|---|---|---|---|---|---|
| Text-based LSTM | 83.21 | 83.85 | 43.38 | 52.45 | 93.44 | 88.90 |
| Multi-Modal CNN | 93.12 | 83.85 | 52.83 | 54.12 | 93.44 | 90.57 |
| The model 230 | 100 | 90.60 | 58.31 | 56.92 | 94.24 | 92.72 |

Even for challenging queries, such as "salt" and "white flour," it is evident across all five exemplary queries that the deep multi-modal pairwise ranking model 230 performs the best among all three models. Furthermore, the rightmost column contains the average NDCG score computed over all 30 queries, which shows that the Multi-Modal LSTM model as the best performer, once again. As can be seen, the deep multi-modal pairwise ranking model 230 works very well even for real-world food search applications.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

Particularly, in some embodiments, a permanent copy of the programming instructions for individual ones of the aforementioned applications utilizing the deep multi-modal pairwise ranking model 230 (e.g., the health tracking program 218 and/or health tracking application 316) may be placed into permanent storage devices (such as e.g., the memory 206 and/or the memory 310) during manufacture thereof, or in the field, through e.g., a distribution medium (not shown), such as a compact disc (CD), or through communication interface 212, 304 from a distribution server (such as the server 200 and/or another distribution server). That is, one or more distribution media having an implementation of the agent program may be employed to distribute the agent and program various computing devices.

The foregoing detailed description of one or more exemplary embodiments of the health tracking system 100 has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of operating a health tracking system having a processor and a database configured to store a plurality of data records, each of the plurality of data records comprising at least a descriptive string and nutritional data regarding a respective consumable item, the method comprising:

receiving, with the processor, a query string;
retrieving, with the processor, a first data record of the plurality of data records and a second data record of the plurality of data records from the database;
generating, with the processor, (i) a first nutrition information vector from the nutritional data of the first data record and (ii) a second nutrition information vector from the nutritional data of the second data record;
generating, with the processor, a third nutrition information vector based on the query string, using an embedding function of a machine learning model, the embedding function being learned in a training process of the machine learning model;
determining, with the processor, which of the first data record and the second data record is more relevant to the query string based at least in part on the first nutrition information vector, the second nutrition information vector, and the third nutrition information vector; and
transmitting, with a transceiver of the health tracking system, a list of data records of the plurality of data records to an electronic device of a user of the health tracking system, the list of data records at least including the first data record and the second data record, a relative sorting of the first data record and the second data record in the list of data records depending on the determination of which of the first data record and the second data record is more relevant to the query string.

2. The method according to claim 1, wherein the embedding function is a second embedding function, the method further comprising generating, with the processor, at least one feature vector using at least one first embedding function of the machine learning model, the at least one first embedding function being learned in the training process of the machine learning model.

3. The method according to claim 2, wherein the at least one feature vector includes (i) a first feature vector based on the descriptive string of the first data record, (ii) a second feature vector based on the descriptive string of the second data record, and (iii) a third feature vector based on the query string.

4. The method according to claim 3, wherein the act of determining which of the first data record and the second data record is more relevant to the query string includes:
determining, with the processor, (i) a first distance between the first feature vector and the third feature vector and (ii) a second distance between the second feature vector and the third feature vector, using a first distance function; and
determining, with the processor, (i) a third distance between the first nutrition information vector and the third nutrition information vector and (ii) a fourth distance between the second nutrition information vector and the third nutrition information vector, using a second distance function.

5. The method according to claim 4, wherein the act of determining which of the first data record and the second data record is more relevant to the query string includes:

determining, with the processor, a first total distance as a sum of the first distance and the third distance;

determining, with the processor, a second total distance as a sum of the second distance and the fourth distance; and determining, with the processor, which of the first data record and the second data record is more relevant to the query string based on a comparison of the first total distance and the second total distance, the first data record being more relevant to the query string if the first total distance is less than the second total distance, the second data record being more relevant to the query string if the second total distance is less than the first total distance.

6. The method according to claim 3, wherein the act of generating the first feature vector, the second feature vector, and the third feature vector includes:

generating, with the processor, (i) a first numeric matrix representing words contained in the descriptive string of the first data record, (ii) a second numeric matrix representing words contained in the descriptive string of the second data record, and (iii) a third numeric matrix representing words contained in the query string; and generating, with the processor, (i) the first feature vector based on the first numeric matrix, (ii) the second feature vector based on the second numeric matrix, and (iii) the third feature vector based on the third numeric matrix, using the at least one first embedding function of the machine learning model.

7. The method according to claim 6, wherein each of the first numeric matrix, the second numeric matrix, and the third numeric matrix are composed of a plurality of one-hot vectors, each representing individual words.

8. The method according to claim 3, wherein the at least one first embedding function and the second embedding function each include a different Long Short Term Memory (LSTM).

9. The method according to claim 1, wherein the act of generating the first nutrition information vector and the second nutrition information vector includes:

forming, with the processor, the first nutrition information vector with values equal to an energy content from the first data record, a fat content from the first data record, a carbohydrate content from the first data record, and a protein content from the first data record; and forming, with the processor, the second nutrition information vector with values equal to an energy content from the second data record, a fat content from the second data record, a carbohydrate content from the second data record, and a protein content from the second data record.

10. The method according to claim 9, wherein the act of generating the first nutrition information vector and the second nutrition information vector includes:

normalizing, with the processor, the energy content, the fat content, the carbohydrate content, and the protein content of the first nutrition information vector and of the second nutrition information vector on one of (i) a per-unit-mass basis, (ii) a per-unit-weight basis, and (iii) a per-unit-volume basis.

11. The method according to claim 1 further comprising:

training, with the processor, the machine learning model using a plurality of training inputs, each training input including (i) a training query string, (ii) a first descriptive string and first nutritional data labeled as corresponding to a relevant candidate, and (iii) a second descriptive string and second nutritional data labeled as corresponding to an irrelevant candidate, parameter values of the at least one embedding function and of the second embedding function being learned during the training.

12. A health tracking system comprising:

a database configured to store a plurality of data records, each of the plurality of data records comprising at least a descriptive string and nutritional data regarding a respective consumable item; and a data processor in communication with the database, the data processor being configured to:

receive a query string;

retrieve from the database a first data record of the plurality of data records and a second data record of the plurality of data records based on the query string;

generate (i) a first nutrition information vector from the nutritional data of the first data record and (ii) a second nutrition information vector from the nutritional data of the second data record;

generate a third nutrition information vector based on the query string, using an embedding function of a machine learning model, the embedding function being learned in the training process of the machine learning model;

determining which of the first data record and the second data record is more relevant to the query string based at least in part on the first nutrition information vector, the second nutrition information vector, and the third nutrition information vector; and transmit a list of data records of the plurality of data records to an electronic device of a user of the health tracking system, the list of data records at least including the first data record and the second data record, a relative sorting of the first data record and the second data record in the list of data records depending on the determination of which of the first data record and the second data record is more relevant to the query string, wherein the query string is a descriptive string of a third data record of the plurality of data records which is logged in food logs of the user one of (i) more than a predetermined number of times and (ii) with more than a predetermined frequency; and wherein the list of data records is presented on the electronic device of the user as recommended data records that are similar to the third data record.

13. The health tracking system according to claim 12, wherein:

the query string is a search string received from the electronic device of the user; and the list of data records is presented on the electronic device of the user as search results.

14. The health tracking system according to claim 12, wherein:

the query string is a descriptive string of a third data record of the plurality of data records which was selected by the user; and the list of data records is presented on the electronic device of the user as recommended data records that are similar to the selected third data record.

15. The health tracking system according to claim 12, the data processor being configured to:

train the machine learning model using a plurality of training inputs, each training input including (i) a training query string, (ii) a first descriptive string and first nutritional data labeled as corresponding to a relevant candidate, and (iii) a second descriptive string and second nutritional data labeled as corresponding to an irrelevant candidate, parameter values of the at least one embedding function and of the second embedding function being learned during the training.

16. The health tracking system according to claim 12, wherein the embedding function is a first embedding function of the machine learning model, and wherein the data processor is further configured to generate (i) a first feature vector based on the descriptive string of the first data record, (ii) a second feature vector based on the descriptive string of the second data record, and (iii) a third feature vector based on the query string, using at least one first embedding function of the machine learning model, the at least one first embedding function being learned in a training process of the machine learning model.

17. A method of operating a health tracking system to train a machine learning model, the method comprising:
   receiving, with a processor of the health tracking system, a plurality of training inputs, each training input including (i) a query string, (ii) a first descriptive string and first nutritional data labeled as corresponding to a correct output, and (iii) a second descriptive string and second nutritional data labeled as corresponding to an incorrect output; and
   for each training input:
      determining, with the processor, (i) a first nutrition information vector from the first nutritional data and (ii) a second nutrition information vector from the second nutritional data;
      generating, with the processor, a third nutrition information vector based on the query string, using an embedding function of a machine learning model;
      determining, with the processor, a hinge loss based at least in part on the first nutrition information vector, the second nutrition information vector, and the third nutrition information vector; and
      adjusting, with the processor, parameter values of the machine learning model based on the hinge loss.

18. The method according to claim 17 further comprising:
   storing, with the processor, a plurality of data records in a database, each of the plurality of data records comprising at least a descriptive string and nutritional data regarding a respective consumable item;
   receiving, with the processor, a search string from a user of the health tracking system;
   providing, with the processor, a list of data records of the plurality of data record from the database to the user based on the search string;
   receiving, with the processor, a selection from the user of a data record from the list of data records; and
   generating, with the processor, at least one training input of the plurality of training inputs based in part on the search string, the list of data records, and the selection from the user.

* * * * *